(12) United States Patent
Johnson, Jr. et al.

(10) Patent No.: US 11,119,097 B2
(45) Date of Patent: Sep. 14, 2021

(54) GRAPHENE-BIOMOLECULE BIOELECTRONIC DEVICES

(71) Applicant: The Trustees of the University of Pennsylvania, Philadelphia, PA (US)

(72) Inventors: Alan T. Johnson, Jr., Philadelphia, PA (US); Ye Lu, Philadelphia, PA (US); Joseph J. Mitala, Rockville, MD (US); Bohdana Discher, Philadelphia, PA (US); Brett R. Goldsmith, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 14/362,798

(22) PCT Filed: Nov. 20, 2012

(86) PCT No.: PCT/US2012/066064
§ 371 (c)(1),
(2) Date: Jun. 4, 2014

(87) PCT Pub. No.: WO2013/085715
PCT Pub. Date: Jun. 13, 2013

(65) Prior Publication Data
US 2014/0308682 A1 Oct. 16, 2014

Related U.S. Application Data

(60) Provisional application No. 61/566,782, filed on Dec. 5, 2011.

(51) Int. Cl.
*G01N 33/543* (2006.01)
*G01N 33/58* (2006.01)

(52) U.S. Cl.
CPC . *G01N 33/54306* (2013.01); *G01N 33/54353* (2013.01); *G01N 33/54373* (2013.01); *G01N 33/582* (2013.01)

(58) Field of Classification Search
CPC ....... G01N 33/54306; G01N 33/54353; G01N 33/582; G01N 33/54373
See application file for complete search history.

(56) References Cited

U.S. PATENT DOCUMENTS

2004/0058457 A1* 3/2004 Huang .................... B82Y 5/00
436/524
2007/0207155 A1* 9/2007 Takizawa ........... C07K 16/2803
424/146.1

(Continued)

FOREIGN PATENT DOCUMENTS

EP         2362459        8/2011
JP     2004-215514 A      5/2004

(Continued)

OTHER PUBLICATIONS

Fu et al., "Metal-enhanced fluorescence of single green fluorescent protein (GFP)," Elsevier, 376 (2008) 712-717.*

(Continued)

*Primary Examiner* — Tracy Vivlemore
*Assistant Examiner* — Nam P Nguyen
(74) *Attorney, Agent, or Firm* — BakerHostetler

(57) ABSTRACT

Provided are devices and methods featuring a nanoelectronic interface between graphene devices (for example, field effect transistors or FETs) and biomolecules such as proteins, which in turn provides a pathway for production of bioelectronic devices that combine functionalities of the biomolecular and inorganic components. In one exemplary application, one may functionalize graphene FETs with fluorescent proteins to yield hybrids that respond to light at wavelengths defined by the optical absorption spectrum of (Continued)

the protein. The devices may also include graphene in electronic communication with a biomolecule that preferentially binds to a particular analyte.

18 Claims, 26 Drawing Sheets

(56) References Cited

U.S. PATENT DOCUMENTS

| | | | |
|---|---|---|---|
| 2008/0160380 | A1 | 7/2008 | Hamrock |
| 2009/0087493 | A1 | 4/2009 | Dai et al. |
| 2010/0285505 | A1 | 11/2010 | Ostermann et al. |
| 2011/0269243 | A1* | 11/2011 | Strano et al. ............... 436/172 |
| 2013/0164859 | A1* | 6/2013 | Johnson et al. ............. 436/501 |
| 2015/0065363 | A1* | 3/2015 | Johnson et al. ............... 506/9 |

FOREIGN PATENT DOCUMENTS

| | | |
|---|---|---|
| JP | 2005-003687 A | 1/2005 |
| JP | 2005-502045 A | 1/2005 |
| JP | 2005-049334 A | 2/2005 |
| JP | 2006-515231 A | 5/2006 |
| JP | 2006-342040 A | 12/2006 |
| JP | 2007-518802 A | 7/2007 |
| JP | 2008-083042 A | 4/2008 |
| JP | 2008-258594 A | 10/2008 |
| JP | 2010-515231 A | 5/2010 |
| JP | 2010-133948 A | 6/2010 |
| JP | 2011-503102 A | 1/2011 |
| JP | 2011-97930 A | 5/2011 |
| WO | WO 2002-037109 | 5/2002 |
| WO | WO 2003/021247 A1 | 3/2003 |
| WO | WO 2004/099307 A2 | 11/2004 |
| WO | WO 2005/070828 A1 | 8/2005 |
| WO | WO2009136978 A2 * | 11/2009 ............ G01N 27/12 |
| WO | WO 2010-096828 | 8/2010 |
| WO | WO 2010/097518 A1 | 9/2010 |
| WO | WO 2012-050646 | 4/2012 |

OTHER PUBLICATIONS

Chidley et al., "A Designed Protein for the Specific and Covalent Heteroconjugation of Biomolecules," Bioconjugate Chem., 2008, 19, 1753-1756.*
Hu et al., "Carbon Nanostructure-Based Field-Effect Transistors for Label-Free Chemical/Biological Sensors", Sensors, vol. 10, pp. 5133-5159, published May 25, 2010.*
Wang et al., "Gold nanoparticles/L-cysteine/graphene composite based immobilization strategy for an electrochemical immunosensor", Anal. Methods, vol. 2, pp. 1692-1697, published Sep. 24, 2010.*
Merriam-Webster, [print retrieved on Jun. 26, 2017], Retrieved on the internet <https://www.merriam-webster.com/dictionary/planar>.*
Heim et al., "Wavelength mutations and posttranslational autooxidation of green protein", Proc. Natl. Acad. Sci., vol. 91, pp. 12501-12504, published Dec. 1994.*
Cognet et al.,"Single metallic nanoparticle imaging for protein detection in cells", PNAS, vol. 100 (No. 20), pp. 11350-11355, published Sep. 30, 2003.*
Lichtenstein et al., "A New Approach to Understanding Biological Control of Quinone Electrochemistry", Publicly Accessible Penn Dissertations. 180, pp. 1-196, published May 17, 2010.*
Xu et al., "Sequence Diversity of Bacillus thuringiensis Flagellin (H Antigen) Protein at the Intra-H Serotype Level", Applied and Environmental microbiology, Sep. 2008, p. 5524-5532, vol. 74, No. 17 (Year: 2008).*
UniProKB, <http://www.uniprot.org/uniprot/Q6EJ98>, print retrieved May 22, 2018. (Year: 2018).*
Shen et al. ("Colvalent attaching protein to graphene oxide via diimide-activated amidation," Colloids and Surfaces B: Biointerfaces, vol. 81, pp. 434-438, published Jul. 22, 2010) (Year: 2010).*
U.S. Appl. No. 14/241,671, filed Jul. 9, 2014, Johnson et al.
Bogdanov et al, "Green Fluorescent Proteins Are Light-Induced Electron Donors," Nat. Chem. Biol., Jul. 2009, 5(7), 459-461.
Chen et al, "Defect Scattering in Graphene," Physical Review Letters, Jun. 12, 2009, 102(23), 236805-1-236805-4.
Dan et al, "Intrinsic Response of Graphene Vapor Sensors," Nano Letters, Mar. 2009, 9(4), 1472-1475.
Geim, A.K. and Novosclov, K.S., "The Rise of Graphene", Nature Materials, Mar. 2007, 6, 183-191.
Goldsmith et al, "Biomimetic Chemical Sensors Using Nanoelectronic Readout of Olfactory Receptor Proteins," Jul. 2011, ACS Nano, 5(7), 5408-5416.
Graff et al, "Synthesis of Nickel-Nitrilotriacetic Acid Coupled Single-Walled Carbon Nanotubes for Directed Self-Assembly With Polyhistidine-Tagged Proteins," Chem. Mater., Feb. 2008, 20(5), 1824-1829.
International Application No. PCT/US2012/66064: International Search Report and Written Opinion dated Jan. 30, 2013.
Lichtenstein, B.R., "A New Approach to Understanding Biological Control of Quinone Electrochemistry", A Dissertation, UMI Dissertation Publishing, ProQuest, LLC, Ann Arbor, MI 48106-1346, 2010, 215 pages.
Liu et al, "A Graphene-Based Broadband Optical Modulator," Nature, Jun. 2, 2011, 474(7349), 64-67.
Lu et al, "DNA Decorated Graphene Chemical Sensors," Appl. Phys. Lett., Aug. 26, 2010, 97(8), 083107.
Mueller et al, "Graphene Photodetectors for High-Speed Optical Communications", Nat. Photon., 2010, 4(5), 297-301, Published Online: Mar. 28, 2010.
Nair et al, "Fine Structure Constant Defines Visual Transparency of Graphene," Science, Jun. 6, 2008, 320(5881), 1308.
Ni et al, "On Resonant Scatterers as a Factor Limiting Carrier Mobility in Graphene," Nano Letters, Aug. 26, 2010, 10(10), 3868-3872.
Sharma et al, "Anomalously Large Reactivity of Single Graphene Layers and Edges toward Electron Transfer Chemistries," Nano Letters, Jan. 7, 2010, 10(2), 398-405.
Xia et al, "Photocurrent Imaging and Efficient Photon Detection in a Graphene Transistor," Nano Letters, Feb. 9, 2009, 9(3), 1039-1044.
Xia et al, "Ultrafast Graphene Photodetector", Nat. Nano, 2009, 4(12), 839-843, Published Online: Oct. 11, 2009.

\* cited by examiner

| Surface functional groups | | Protein functional groups | Product | |
|---|---|---|---|---|
| NHS ester[136-138] |  | $H_2NR$ |  | amide |
| aldehyde[7,8,133-138] |  | $H_2NR$ |  | imine |
| isothiocyanate[9] |  N=C=S | $H_2NR$ |  | thiourea |
| epoxide[18,139,140] |  | $H_2NR$ |  | aminoalcohol |
| amine[121,132]k |  —NH$_2$ | $HO(O)CCH_2R$ |  | amide |

GRAPHENE-BIOMOLECULE BIOELECTRONIC DEVICES

CROSS-REFERENCE TO RELATED APPLICATIONS

This application is the National Stage of International Application No. PCT/US2012/066064, filed Nov. 20, 2012, which claims the benefit of and priority to U.S. Provisional Application No. 61/566,782, filed Dec. 5, 2011, the entireties of which applications are incorporated herein by reference for any and all purposes.

GOVERNMENT RIGHTS

This invention was made with government support under Grant Numbers IGERT DGE-0221664 and NSEC DMR08-32802 awarded by the National Science Foundation. The government has certain rights in the invention.

TECHNICAL FIELD

The present disclosure relates to the fields of graphene materials, bioelectronic devices, and proteins.

BACKGROUND

Graphene has drawn attention for its electronic, mechanical and thermal properties, and also has potential for use in optical and optoelectronic applications, e.g, ultrafast photo-detectors and optical modulators. For photo-detectors or -absorbers, it is desirable to tune the wavelength of the device response. This application of graphene is problematic, however, as graphene monolayers show constant absorption of $\pi\alpha=2.3\%$, where a is the fine structure constant, across the visible and infrared range. Accordingly, there is a long-felt need for graphene-based optoelectronic devices.

SUMMARY

In meeting these long-felt needs, the present disclosure provides devices, comprising a biomolecule in electronic communication with a graphene body, the biomolecule having an optical absorption peak at around a particular wavelength of excitation illumination.

The disclosure also provides methods, the methods including contacting a biomolecule to a graphene body such that the biomolecule and graphene body are placed into electronic communication with one another.

Also provided are devices, the devices including a graphene body in electronic communication with a biomolecule that preferentially binds a binding partner, the graphene body being in electronic communication with a biomolecule capable of detecting a change in an electronic characteristic of the biomolecule.

Further provided are methods, the methods including illuminating a device with a wavelength of illumination, the device comprising a photosensitive protein having an optical absorption peak at around a particular wavelength of illumination, the photosensitive protein being in electronic communication with a body of graphene; and detecting a change in an electronic characteristic of the device.

Also provided are methods, the methods including contacting a sample to a device comprising a graphene body in electronic communication with a biomolecule that preferentially binds a binding partner, the graphene body being in electronic communication with a device capable of detecting a change in an electronic characteristic of the protein; and monitoring a change in an electronic characteristic of the device related to binding between the biomolecule and binding partner.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale or proportion. In the drawings:

FIG. 1D Schematic of chemical coupling between graphene (bottom) and the protein's histidine tag (top).

FIG. 3A Responses of GFP-GFET. Beginning at time 100 sec, the sample is illuminated for 50 sec and then the light is turned off for 50 sec. Only violet illumination causes a detectable response. Inset: Measured absorption spectrum of GFP. The wavelengths used in the experiments are indicated by appropriately colored dots. FIG. 3B Photocurrent responses of YFP-GFET hybrid. Beginning at time 50 sec, the sample is illuminated for 50 sec and then the light is turned off for 50 sec. Now only green illumination produces a detectable response. Inset: Measured absorption spectrum of YFP with dots indicating wavelengths used.

FIG. 4C Height profile of linescans shown in FIG. 4A black and FIG. 4B blue.

FIG. 6B Height profile of linescan shown in FIG. 6A.

FIG. 7C Height profile of linescans shown in FIG. 7A black and FIG. 7B blue.

DETAILED DESCRIPTION OF ILLUSTRATIVE EMBODIMENTS

Figure 1A:
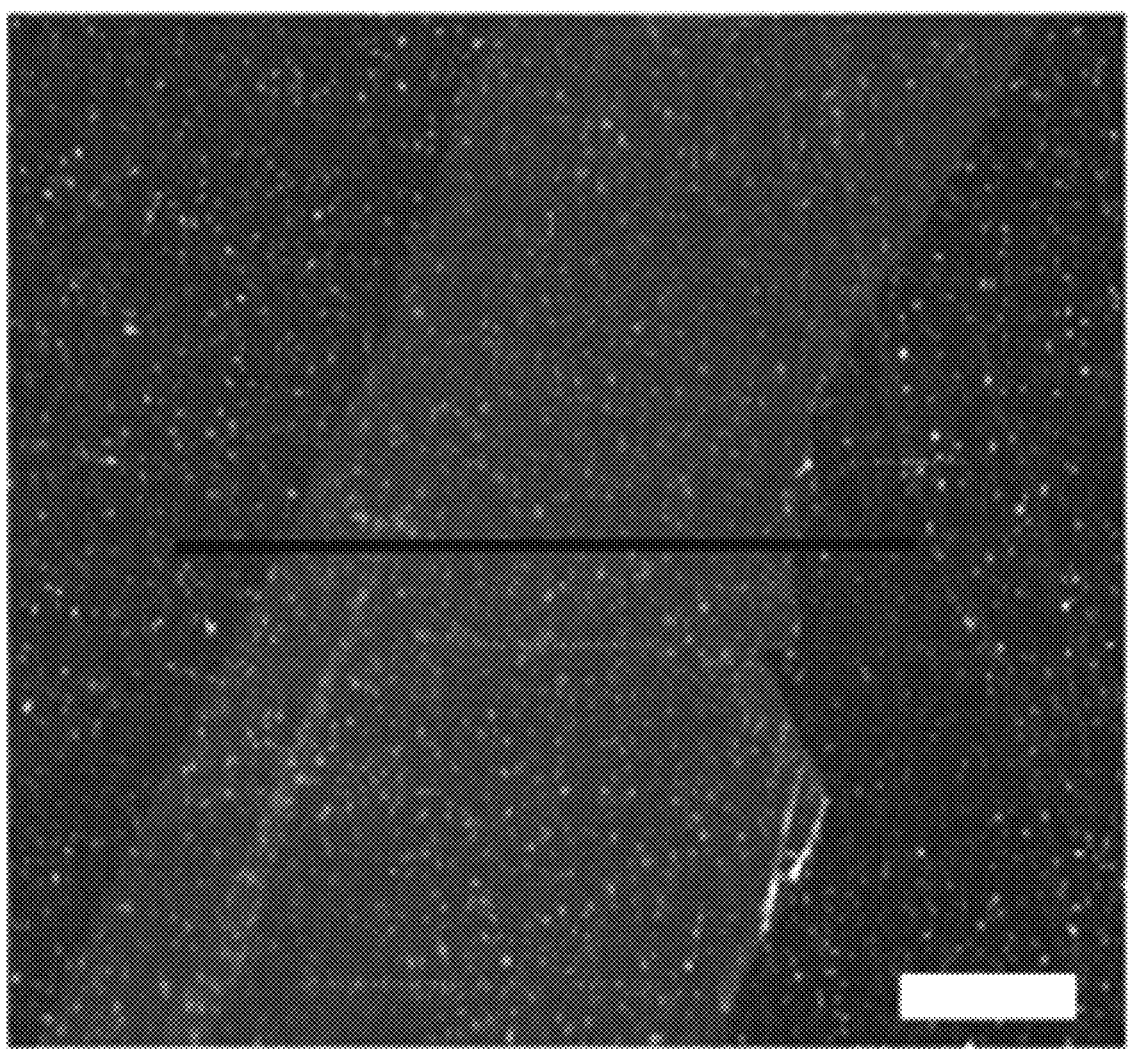
FIGS. 1A-1D illustrates an AFM of monolayer graphene before FIG. 1A and after FIG. 1B functionalization with His-tagged protein G (1 μm scale bar for both images); z-scales are 8 nm and 20 nm, respectively), FIG. 1C Height linescans indicated on FIG. 1A and FIG. 1B.

The present invention may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. The term "plurality," as used herein, means more than one. When a range of values is expressed, another embodiment includes from the one particular value and/or to the other particular value. Similarly, when values are expressed as approximations, by use of the antecedent "approximately" or "about," it will be understood that the particular value forms another embodiment. All ranges are inclusive and combinable, and all documents cited herein are incorporated by reference in their entireties for any and all purposes.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range.

Presented here are devices and related methods that place optically active biomolecules (e.g., proteins) into electronic communication with graphene, as well as devices and methods that place biomolecules (e.g., proteins) with analyte recognition capabilities into electronic communication with graphene. Such biomolecules include olfactory receptors, antibodies or even antibody fragments capable of detection of disease biomarkers. Enzymes are also suitable biomolecules for use in the disclosed devices and methods. The specificity of the interaction between enzymes and their substrates makes enzymes particularly suitable for use in the disclosed devices and methods.

The present disclosure first presents devices, the devices including a biomolecule in electronic communication with a graphene body, the biomolecule having an optical absorption peak at around a particular wavelength of excitation illumination.

Proteins, antibodies, and antibody fragments, are considered particularly suitable biomolecules for the disclosed devices. The biomolecule (e.g., protein) may be one that preferentially binds to one or more binding partners. Antibodies, enzymes, ligands, and receptors are considered particularly suitable for this purpose. It should be understood that biomolecules used the disclosed devices and methods may be isolated from nature or be synthetic in nature.

A protein or other biomolecule used in the devices may include a histidine tag. Histidine-facilitated binding between proteins and graphene is considered especially suitable, but is not the only way in which biomolecules and graphene may be placed into electronic communication with one another. In some embodiment, such as those shown in the attached exemplary figures, electronic communication between the biomolecule and the graphene body includes an interaction between a nickel-nitriloacetic acid group and a histidine residue.

In some embodiments, a protein may be bound to graphene by a peptide sequence. In one embodiment, a protein may be attached to graphene by adding a specific peptide sequence, such as one that is identified using a phase display peptide library.

Graphene may itself be modified to comprise a moiety to facilitate attachment. Such moieties include sugars, antibodies, a chitin binding protein, a maltose binding protein, glutathione-S-transferase (GST), an epitope tag, and the like. Suitable epitope tags include a V5-tag, a c-myc-tag, a HA-tag, or any combination thereof. Proteins used in the disclosed devices may include a reactive amino acid, which includes photoreactive amino acids.

The graphene of the disclosed devices may include a diimide-activated amidation between the graphene and biomolecules. The devices may also include a cysteine-graphene linkage between the graphene and biomolecules. Such a linkage may be effected by treatment with diazonium, EDC NHS, PDEA aka 2-(2-pyrdinyldithio) ethaneamine, with a thiol-bearing region of the protein.

Figure 13:
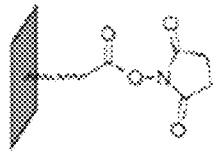
FIG. 13 illustrates exemplary schemes for attaching proteins or other biomolecules to graphene substrates.
Figure 13:
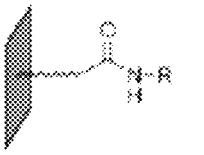
Figure 13:
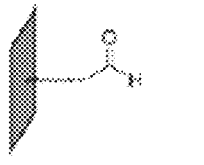
Figure 13:
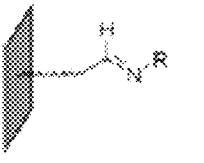
Figure 13:
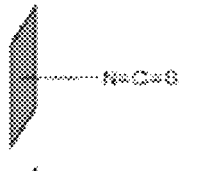
Figure 13:
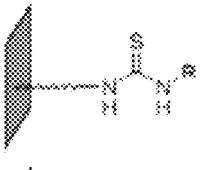
Figure 13:
Figure 13:
Figure 13:
Figure 13:

A variety of linkages may be used to connect a biomolecule to graphene. Certain exemplary linkages and chemistries are shown in FIG. 13, and include an amide bond between the biomolecules and graphene, an imine bond between the biomolecule and graphene, a thiourea bond between the biomolecule and graphene, an aminoalcohol bond between the biomolecule and graphene.

In embodiments where the biomolecule comprises a protein, the protein may be a fluorescent protein, a fusion protein, or both. A fluorescent protein may be a green fluorescent protein, a yellow fluorescent protein, a red fluorescent protein, a cyan fluorescent protein, or any combination thereof. A protein may include a fluorescent redox cofactor. A protein may include a flavoprotein, a heme containing protein wherein an iron has been substituted by zinc, and the like. A protein may include tryptophan, which is known to fluoresce.

The wavelength of excitation illumination for the biomolecule may be between 1 nm and about 1500 nm, or even between about 200 and 900 nm, or between 300 and 700 nm. Various proteins have different excitation peak wavelengths: Green fluorescent protein: 400 nm; Enhanced green fluorescent protein: 488 nm; Yellow fluorescent protein: 525 nm; Red fluorescent protein: 557 nm; Cyan fluorescent protein:

458 nm; Tryptophan containing proteins: 280 nm; flavin mononucleotide containing proteins: 450 nm. Proteins may have one, two, or more wavelengths.

The graphene of the disclosed devices may be a sheet, a ribbon, a cylinder, a platelet, or virtually any other configuration. The graphene may be single-atom thickness or may have a thickness of multiple atoms. The graphene may thus comprise multiple sheets. The graphene of the devices is suitably in electronic communication with a device that monitors an electronic characteristic of the graphene body.

Also provided are methods. These methods include contacting a biomolecule to a graphene body such that the protein and graphene body are placed into electronic communication with one another. The biomolecule and graphene bodies suitably comprise one or more moieties that bind to one another, coordinate with one another, or both. The biomolecule (e.g., protein) may include a histidine residue, which histidine residue may interact with one or more molecules associated with the graphene, which molecule may be a metal.

The methods may include one or more carboxylic acid groups on the graphene body. The user may also attach a sugar, an antibody, a chitin binding protein, a maltose binding protein, glutathione-S-transferase (GST), an epitope tag, and the like to graphene. In some embodiments, such as those shown in the exemplary figures attached hereto, the electronic communication between the protein and the graphene body includes an interaction between a nickel-nitrilo-acetic acid group and a histidine residue.

The present disclosure also provides additional devices. These devices suitably include a graphene body in electronic communication with a biomolecule that preferentially binds a binding partner, with the graphene body being in electronic communication with a device capable of detecting a change in an electronic characteristic of the biomolecule.

The biomolecule is suitably a protein. The protein suitably features recognition capabilities for other proteins (e.g., cancer biomarkers) or for molecules in the environment. Olfactory receptors or other proteins that bind small molecules are considered especially suitable for such applications. Receptors, ligands, antibodies, antigens, enzymes, or even antibody fragments are all considered suitable biomolecules for these devices. The user may place the graphene into electronic communication with a device that monitors changes in an electronic characteristic of the device. In this way, when a target binds to the biomolecule that is in electronic communication with the graphene, an associated change in an electronic characteristic of the device (e.g., conductivity/resistance) is detected and registered. As one example, a device according to the present disclosure that includes an antibody complementary to antigen X may be contacted to a sample that may or may not contain antigen X. If antigen X is present, the antigen will bind to the antibody. The binding will in turn change an electronic characteristic of the device, which will then be registered by the device. If the antigen is not present in the sample, the electronic characteristics of the device will remain constant, and the user will understand that the analyte is not present.

The devices may be constructed so as to include one, two, or more biomolecule detectors in electronic communication with graphene. The biomolecules may differ in terms of their binding affinities for different analytes, thus allowing for the construction of devices capable of simultaneously detecting the presence of two or more analytes. The devices are also capable of providing multiple biomolecules for detecting the same analyte, thus providing some redundancy in the device.

Also provided are methods. These methods include illuminating a device with a wavelength of illumination, the device comprising a photosensitive protein having an optical absorption peak at around a particular wavelength of illumination, the photosensitive protein being in electronic communication with a body of graphene; and detecting a change in an electronic characteristic of the device. Suitable proteins are described elsewhere herein; fluorescent proteins are considered especially suitable. The user may also contact the protein to a sample. Such samples may include a binding partner complementary to the protein, such as other proteins and other analytes. For example, as described elsewhere herein, the user may contact a device having an antibody bound to graphene to a sample that may contain an analyte complementary to the antibody. The user may then detect a change in an electronic characteristic (e.g., conductivity) related to binding between the antibody and analyte.

A user may also contact a sample to a device comprising graphene body in electronic communication with a biomolecule that preferentially binds a binding partner, the graphene body being in electronic communication with a device capable of detecting a change in an electronic characteristic of the protein; and monitoring a change in an electronic characteristic of the device related to binding between the biomolecule and binding partner.

With regard to particular embodiments of the disclosed methods and devices, when a fluorescent protein with an optical absorption peak at a particular wavelength is used, the graphene field effect transistor (GFET) provides sensitive all-electronic readout of the protein's optical excitation. The approach thus enables creation of a family of bio/nano hybrid photodetectors, each sensitive to a wavelength range defined by proteinaceous components. The use of proteins with different functionalities (e.g., chemical affinity for particular biomarkers or small molecules in the liquid or vapor phase) allows for suitable use in various applications, e.g., medical diagnostics, homeland security.

Exemplary experiments were performed on graphene produced by mechanical exfoliation onto oxidized silicon substrates. Graphene monolayers were selected by inspection with Atomic Force Microscopy (AFM) and Raman spectroscopy. Devices were functionalized with carboxylated diazonium salts, which readily form covalent bonds with graphene. Additional information relevant to functionalization is found in international patent application PCT/US2011/042290 and in U.S. patent application 61/529,341, both of which are incorporated herein by reference in their entireties for any and all purposes.

As done for protein-carbon nanotube hybrids, the resulting carboxylic acid groups were activated with 1-ethyl-3-[3-dimethylaminopropyl]carbodiimide hydrochloride/sulfo-N-hydroxysuccinimide (EDC/sNHS), followed by attachment of nitrilotriacetic (NTA). Device fabrication was completed by adding Ni ions to the NTA complex, and incubation in protein solution (see FIG. 1D). Histidine-tagged proteins obtained commercially (protein-G (26.1 kDa), green fluorescent protein (GFP), and yellow fluorescent protein (YFP)) and a fusion protein were all successfully attached to graphene devices, illustrating the robustness and versatility of the approach. The His-tagged (recombinant) fusion protein is comprised of glutathione S-transferase (GST), 6 histidine residues, and "BT5", an artificial heme binding protein.

Figure 1B:
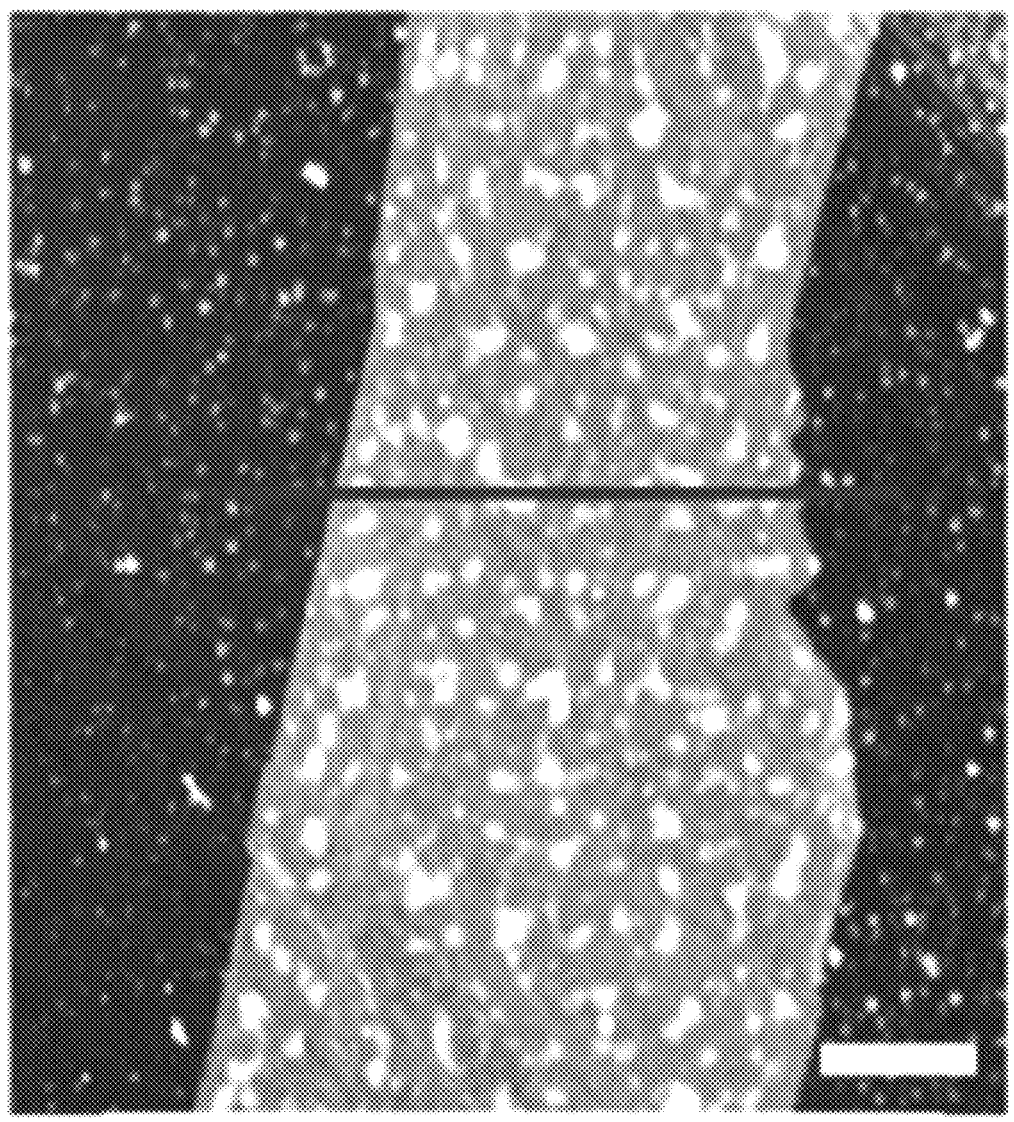
Figure 1C:
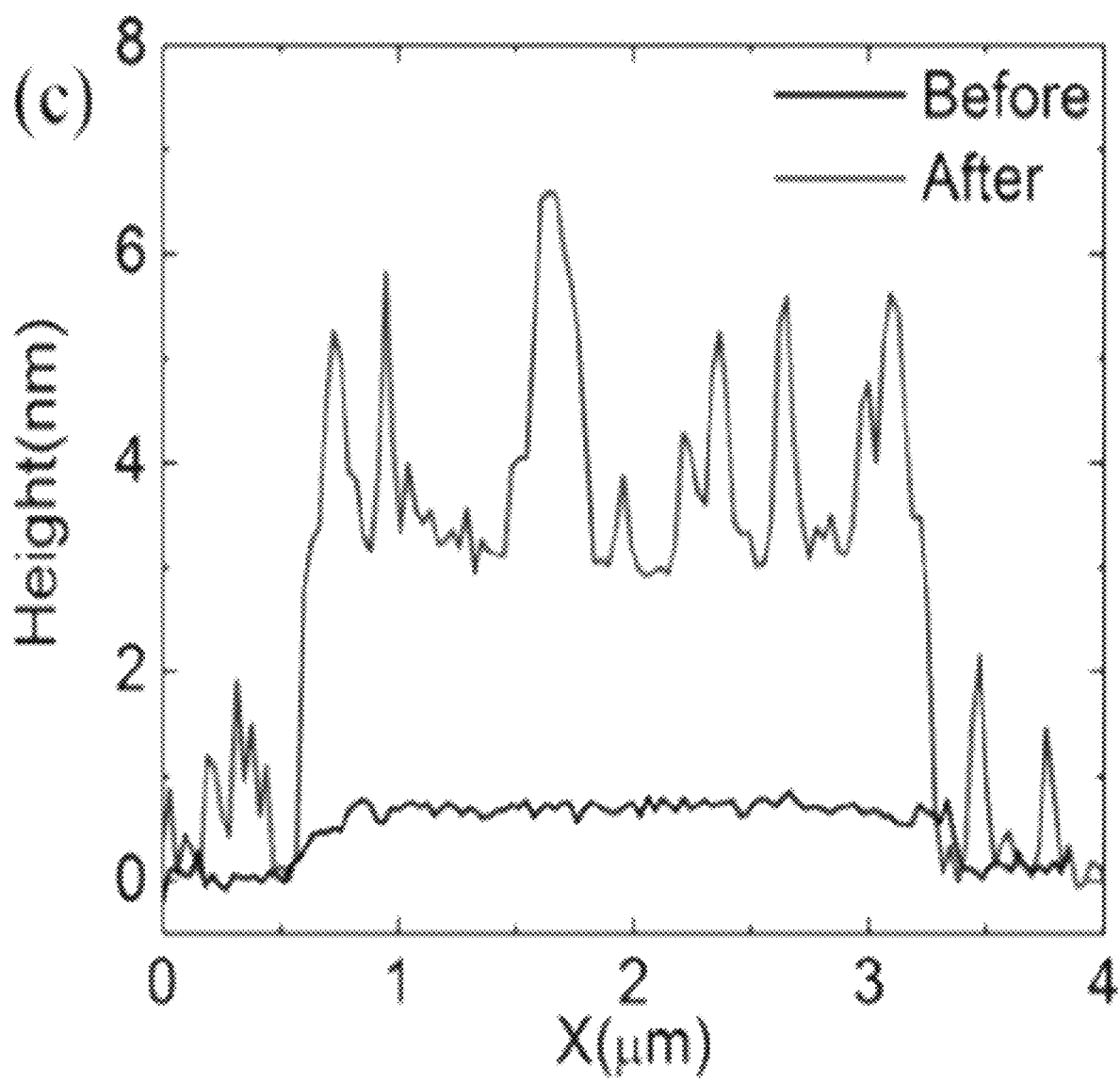
Figure 1D:
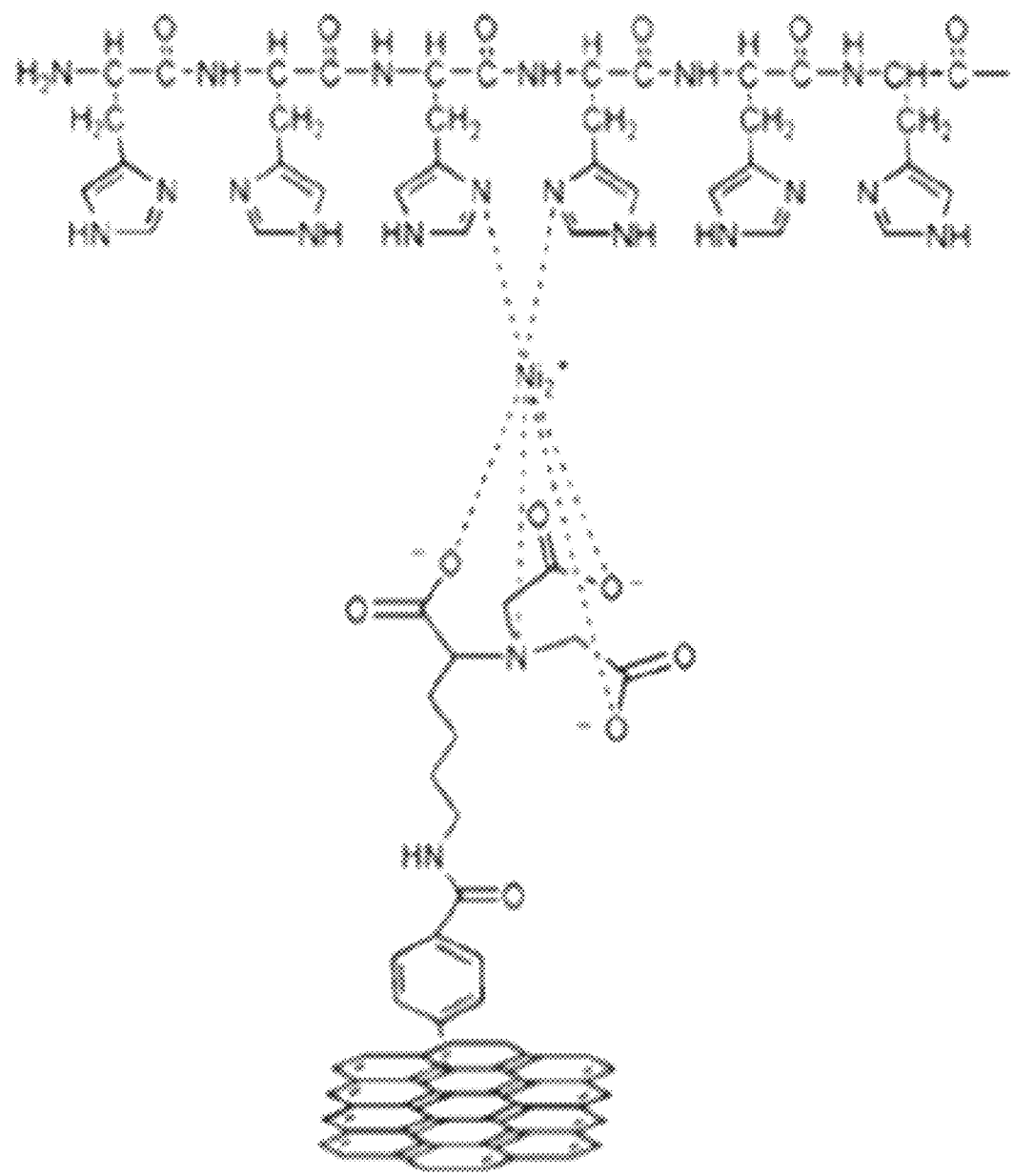

FIGS. 1A and 1B are AFM images of the same graphene monolayer before and after functionalization with His-tagged protein-G, while FIG. 1C shows height profiles along the indicated linescans. Two changes are observed: a 2-nm increase in baseline height of the functionalized graphene, and the appearance of particles of height 3.4±0.4 nm above the new baseline. In other experiments, AFM of graphene monolayers before and after incubation in diazonium solution showed height increases of 0.5-nm height, in agreement with earlier reports. A ~2-nm height increase was found upon attachment of NTA, with no particles observed (data not shown). Without being bound to any single theory, one may associate the increased baseline height in FIG. 1B with a NTA layer and the particles with proteins bound by the His-tags. The claim of control over protein orientation in the hybrid and the device structure of FIG. 1D were confirmed by additional experiments—if the diazonium step were omitted, no molecules are found on the graphene surface, and if the protein lacks a His-tag, they do not bind to the Ni-NTA molecular layer.

Figure 2:
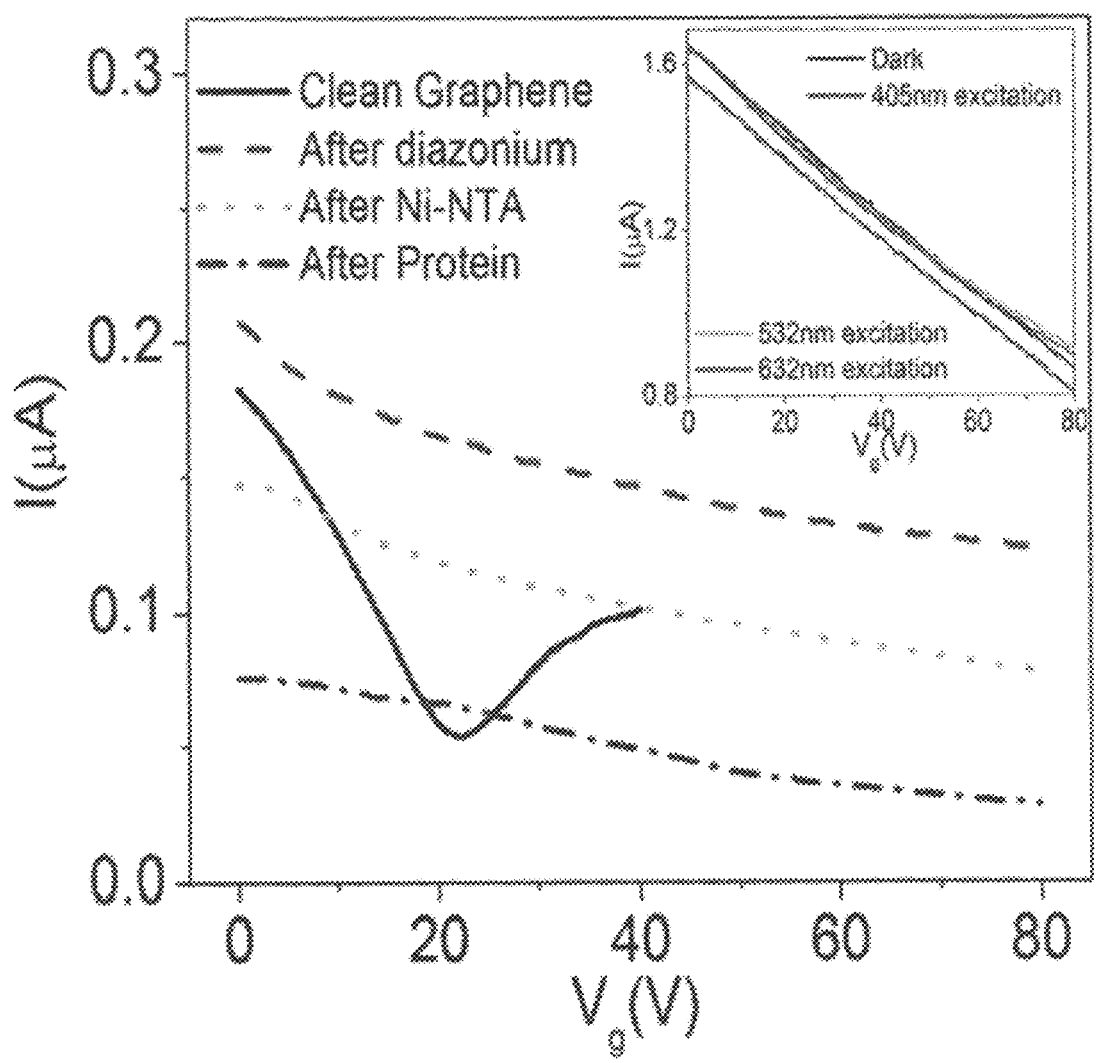
FIG. 2 presents current-gate voltage characteristic ($I-V_G$) of graphene FET after each step required for functionalization with fusion protein GST-BTS: as prepared (black), after diazonium treatment (red dashed), after Ni-NTA attachment (green dotted), and after incubation in protein (GST-BT5) solution (blue dot-dash). Bias voltage is 1 mV. (Inset) $I-V_G$ characteristics of a GFP-GFET with different illumination conditions: no illumination (black), and illumination at 405 nm (violet data), 532 nm (green data), and 632 nm (red data). Illumination intensity is approximately 70 mW/cm² for each wavelength. Bias voltage is 10 mV.

For bio/nano hybrid devices, GFETs were fabricated using electron beam lithography. Care was taken to remove unwanted residues by thermal annealing. FIG. 2 shows current-gate voltage ($I$-$V_G$) data from a GFET before and after subsequent processing steps resulting in attachment of fusion protein GST-BTS. Annealed GFET $I$-$V_G$ shows ambipolar behavior and carrier mobility of ~2000 $cm^2$/V-s for holes and electrons. The neutrality point ($V_N$) occurs at gate voltage ~20V, corresponding to a doped carrier density of $1.6\times10^{12}/cm^2$ at $V_G$=0. After diazonium treatment (dashed data), the device appears p-type with hole mobility ~300 $cm^2$/Vs; and $V_N$ exceeds 80V, the maximum gate voltage used. The carrier mobility decrease is attributed to defects formed by $sp^2$ bond breaking and attached carboxybenzene groups; increased D-band intensity seen in the Raman spectrum supports this picture. The $V_N$ shift is consistent with increased negative charge in the graphene environment, due to deprotonation of bound carboxybenzene groups in a nanoscale water layer formed under ambient. Subsequent attachment of Ni-NTA (blue dashed line) and GST-BT5 (green dotted line) does not affect the carrier mobility but the GFET conductance drops by ~25%, consistent with increased carrier scattering by bound molecules.

Protein-GFET bio/nanohybrid combines functionality of both components. Integration of photoactive proteins create hybrids with photoresponses tuned to desired wavelength ranges.

FIG. 2(inset) shows $I$-$V_G$ data for GFP-GFET hybrid measured in the dark and when exposed to light of three different wavelengths (405 nm, 532 nm and 632 nm, referred to as violet, green, and red) at 70 mW/$cm^2$ intensity. A significant $I$-$V_G$ shift is observed only for violet illumination, with negligible change for green or red light. This wavelength-dependent photoresponse is consistent with the optical absorption spectrum of GFP, which is peaked near 400 nm with little absorption for wavelengths greater than 500 nm (inset to FIG. 3A; colored dots indicate wavelengths used). One may attribute the $I$-$V_G$ shift to a GFET electronic response to the photoexcitation of GFP. The observed current decrease may reflect a net dipole associated with charge redistribution in GFP upon photoexcitation, or GFP-GFET charge transfer since GFP is reported to be a light induced electron donor.

Figure 3A:
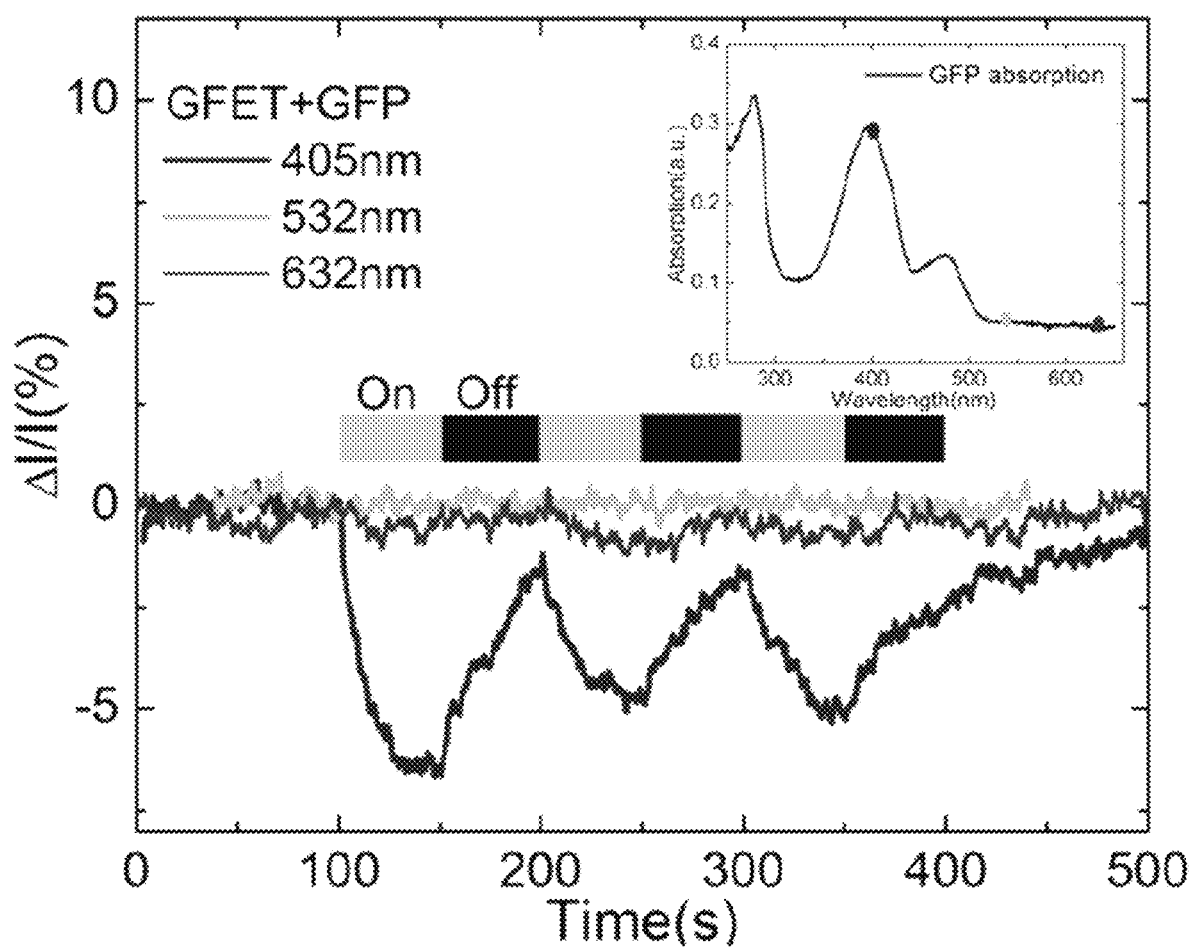
FIGS. 3A-3B presents photocurrent responses (% ΔI/I) of GFET hybrids incorporating green and yellow fluorescent protein (GFP and YFP, respectively) are determined by the proteins' optical absorption spectra. Responses are shown to illumination at 405 nm (violet data), 532 nm (green data), and 632 nm (red data).
Figure 3B:
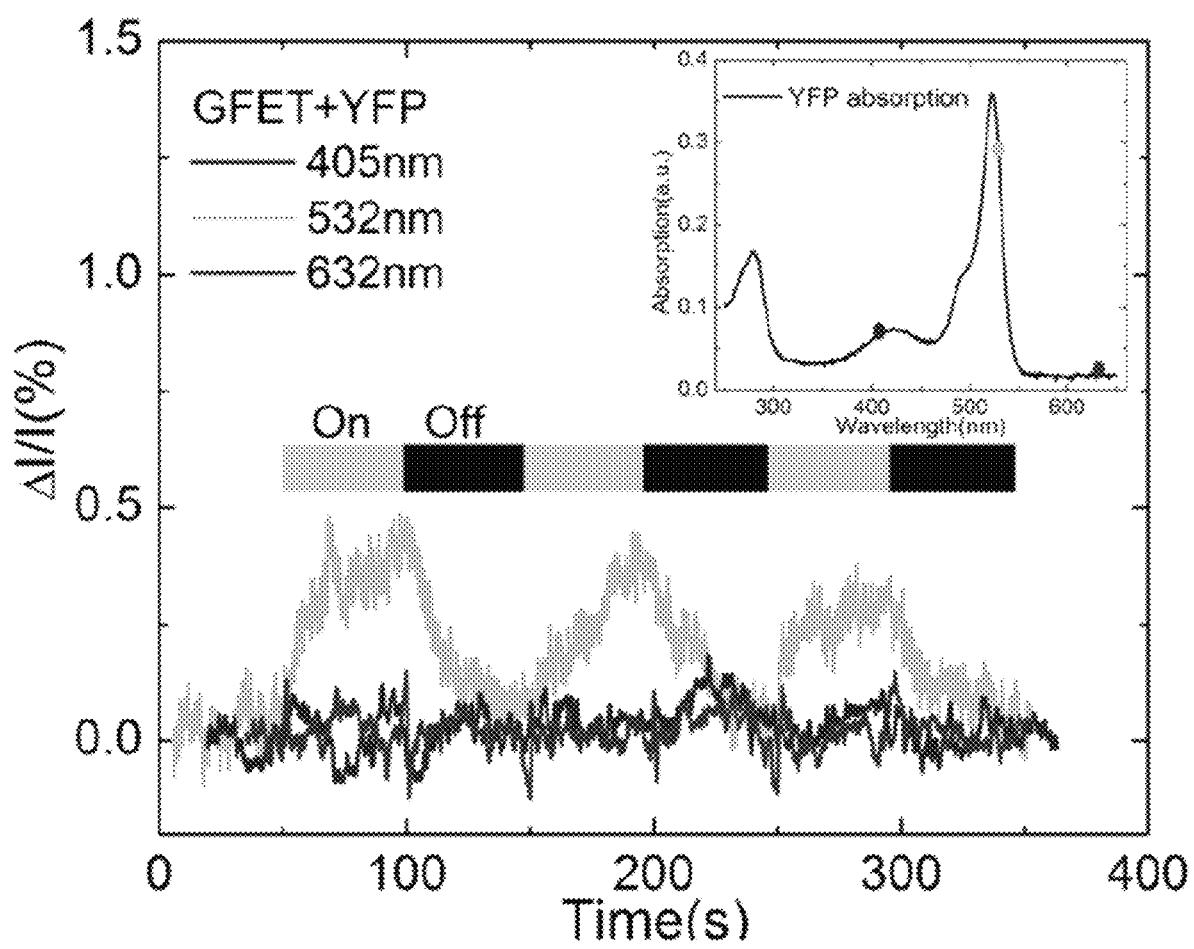

Data in FIGS. 3A-3B provide information concerning bio/nano hybrids whose photocurrent response is determined by the optical properties of the protein component. Measurements were performed under ambient at $V_G$=0 and $V_B$=10 mV. In FIG. 3A, starting at time 100 sec GFP-GFET hybrid was illuminated for 50 sec with light of a particular wavelength, and then the light was quenched for 50 sec; three cycles were used to gauge reproducibility. The response is shown as fractional change in DC current from the dark current baseline. For green and red illumination, the photoresponse is within the system noise (<0.1%). In contrast, violet illumination induces a clear response of approximately −6%. It was shown that the wavelength of maximum hybrid device photoresponse is controlled by choice of fluorescent protein. For a yellow fluorescent protein (YFP)-GFET hybrid (FIG. 3B), strong conduction modulation occurs when the device is illuminated in the green, while excitation with violet or red light produces negligible response, as anticipated by the absorption spectrum of YFP (FIG. 3B, inset). FP-GFET devices are stable, with lifetimes exceeding two weeks.

The disclosed methods are robust and reproducible processes for bind His-Tagged proteins to graphene FETs. This in turn provides a pathway for construction of bio/nano hybrids integrating desirable functionalities of both components. AFM, Raman spectroscopy, and control experiments were used to confirm the hybrid structure, and transport measurements to assess electronic effects of protein attachment.

As an example of the capabilities enabled by the method, it was demonstrated that FP-GFET hybrids present a new class of tunable photodetectors with photocurrent responses in a wavelength range determined by the absorption spectrum of the bound FP.

Exemplary Materials and Methods

The following are illustrative embodiments of the disclosed devices and methods. These are illustrative only and do not limit the scope of the present disclosure.

1. Protein Functionalization Scheme

Figure 12:
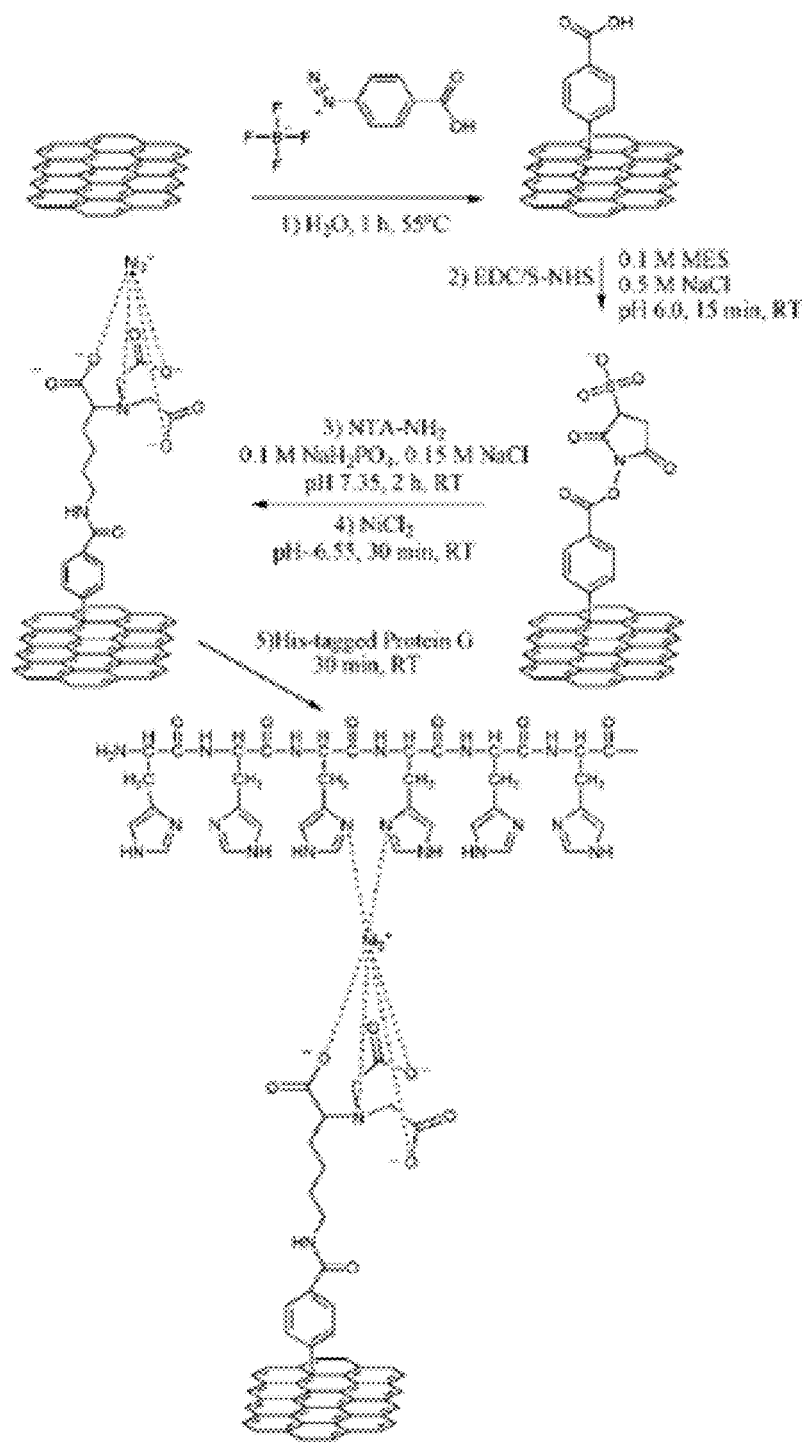
FIG. 12 illustrates an exemplary reaction scheme for functionalization of graphene with Polyhistidine-Tagged Protein.

FIG. 12 illustrates an exemplary functionalization process. Monolayer graphene on an oxidized silicon substrate was decorated with covalently bound carboxybenzene groups by immersion in a solution of 10.76 mM 4-carboxybenzene diazonium tetrafluoroborate (Best West Laboratories, Inc) at 55° C. for 1 h, followed by rising with acetone, methanol, and deionized (DI) water in sequence. The chips were then incubated in a solution of 2 mM EDC (Sigma)/5 mM Sulfo-NHS (Thermo Scientific) activation buffer (0.1 M 2-(N-Morpholino)ethanesulfonic acid (MES) sodium salt, 0.5 M NaCl, pH adjusted to 6.0 with HCl) at room temperature for 15 min to activate the carboxylic acid of the carboxybenzene. Immediately afterwards, the chips were washed with activation buffer and placed in a solution of 11.3 mM Nα,Nα-Bis(carboxymethyl)-L-lysine hydrate (NTA-NH2 (Aldrich)) prepared with phosphate buffered saline (PBS; 0.1 M NaH2PO4, 0.15 M NaCl, pH adjusted to 7.35 with NaOH) for 2 h. Upon completion, the chips were washed with water and placed in a solution of 11.3 mM NiCl2 (Aldrich) for 30 minutes, rinsed in DI-water, and blown dry.

His-tagged protein solution was pipetted onto the surface of the chips, followed by incubation for 30 min at room temperature. The solution droplet was large enough so that any volume change over the 30 min period due to evaporation was negligible. The chip was then rinsed with DI water to remove non-specifically bound proteins and blown dry.

GFP was purchased from Millipore Corporation, and YFP was purchased from MBL International. His-tagged protein G was purchased from bio-World, and non his-tagged protein G for control experiments was purchased from ProSpec-Tany TechnoGene Ltd.

2. AFM of Graphene at Different Stages of the Functionalization Scheme

2.1 AFM of Graphene after Incubation in Diazonium Salt Solution

Figure 4A:
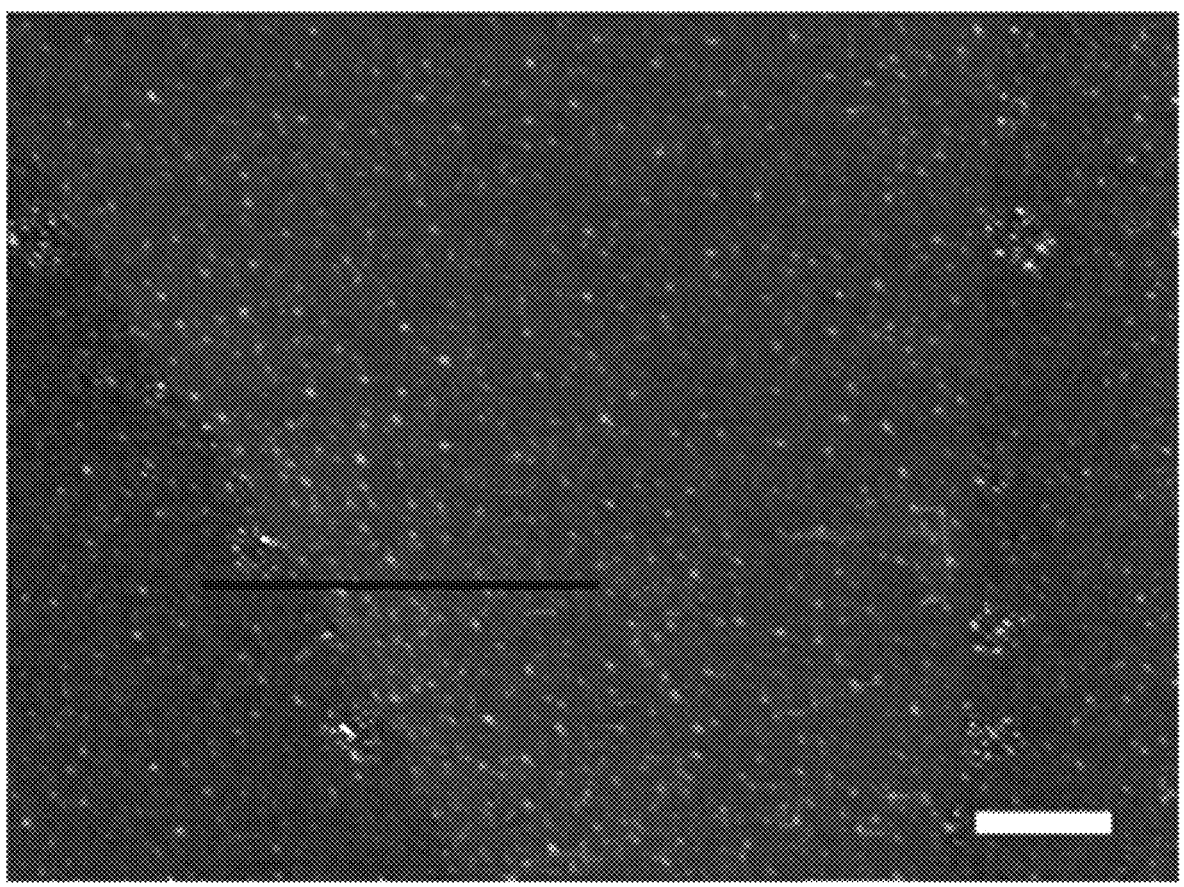
FIGS. 4A-4C presents AFM images of a monolayer graphene FIG. 4A before and FIG. 4B after incubation in 4-carboxybenzene diazonium tetrafluoroborate solution. The z scale is 10 nm.
Figure 4B:
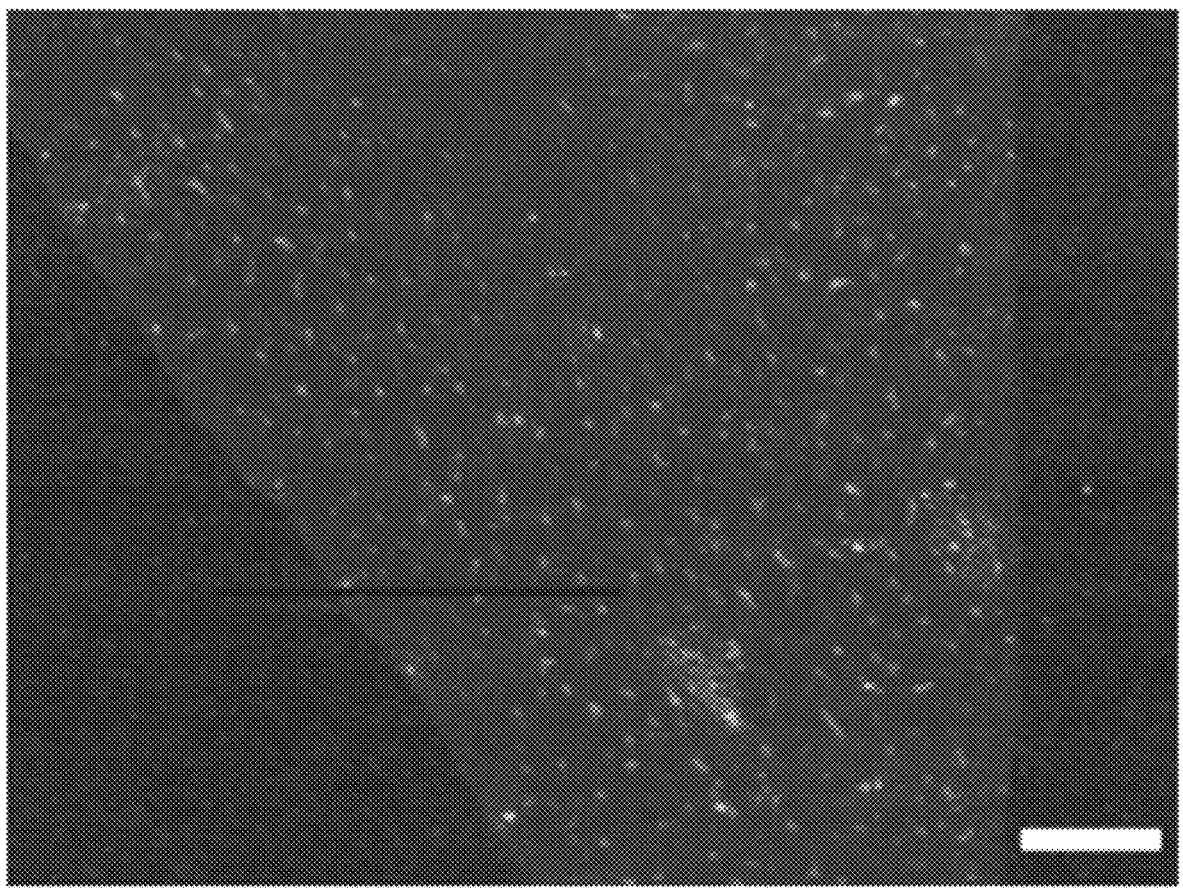
Figure 4C:
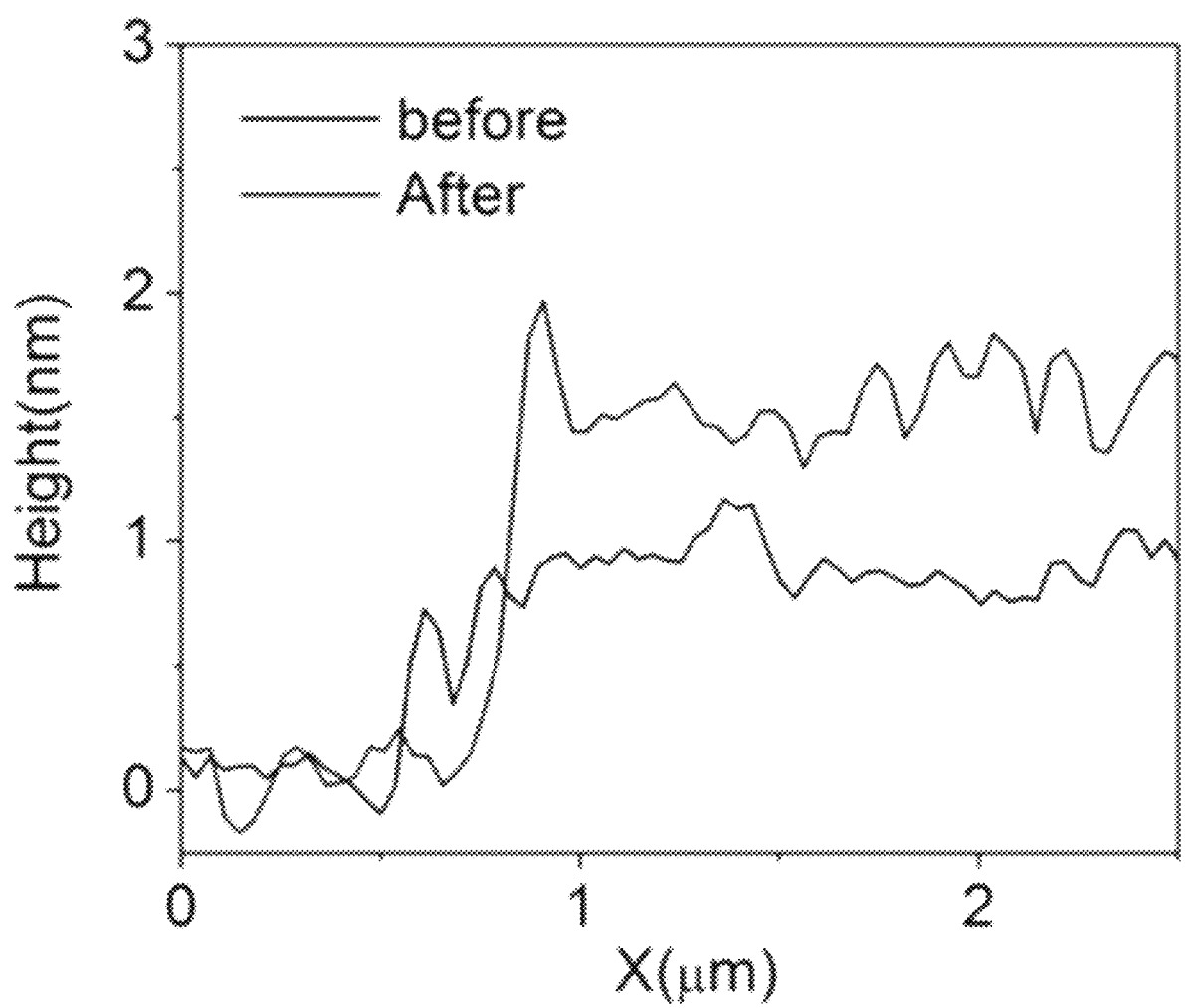

A monolayer graphene sample was incubated in 4-carboxybenzene diazonium tetrafluoroborate salt solution in a water bath at 55° C., as discussed above. FIGS. 4A and 4B provide AFM images of graphene before (FIG. 4A) and after (FIG. 4B) functionalization. The apparent height of the graphene is increased by ~0.5 nm (associated with the carboxybenzene group; see FIG. 12), and the surface is somewhat rougher.

Figure 5A:
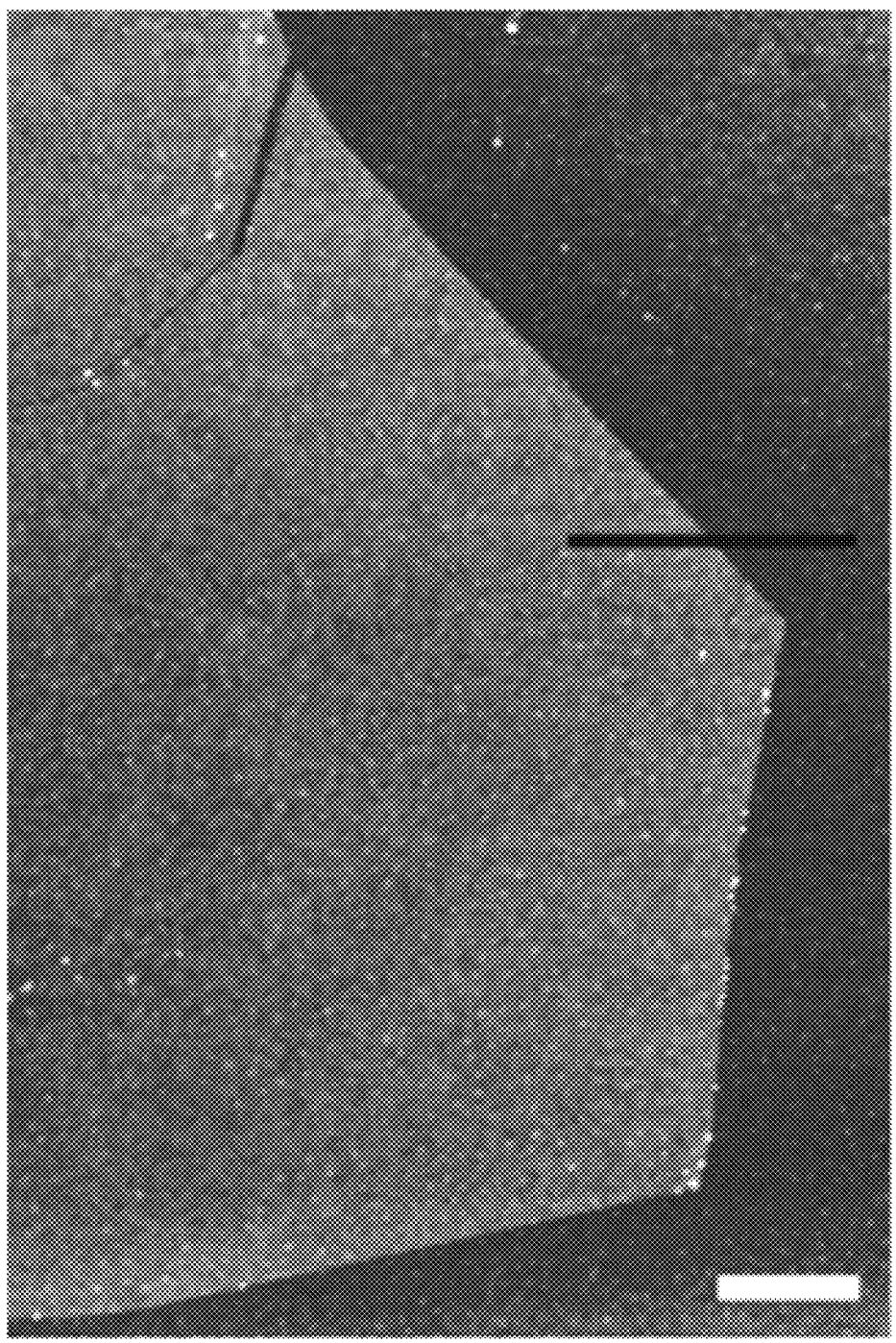
FIG. 5 presents AFM images of graphene (a) before and (b) after all functionalization steps except protein incubation. Z-scale is 15 nm. (c) Associated height linescans.
Figure 5B:
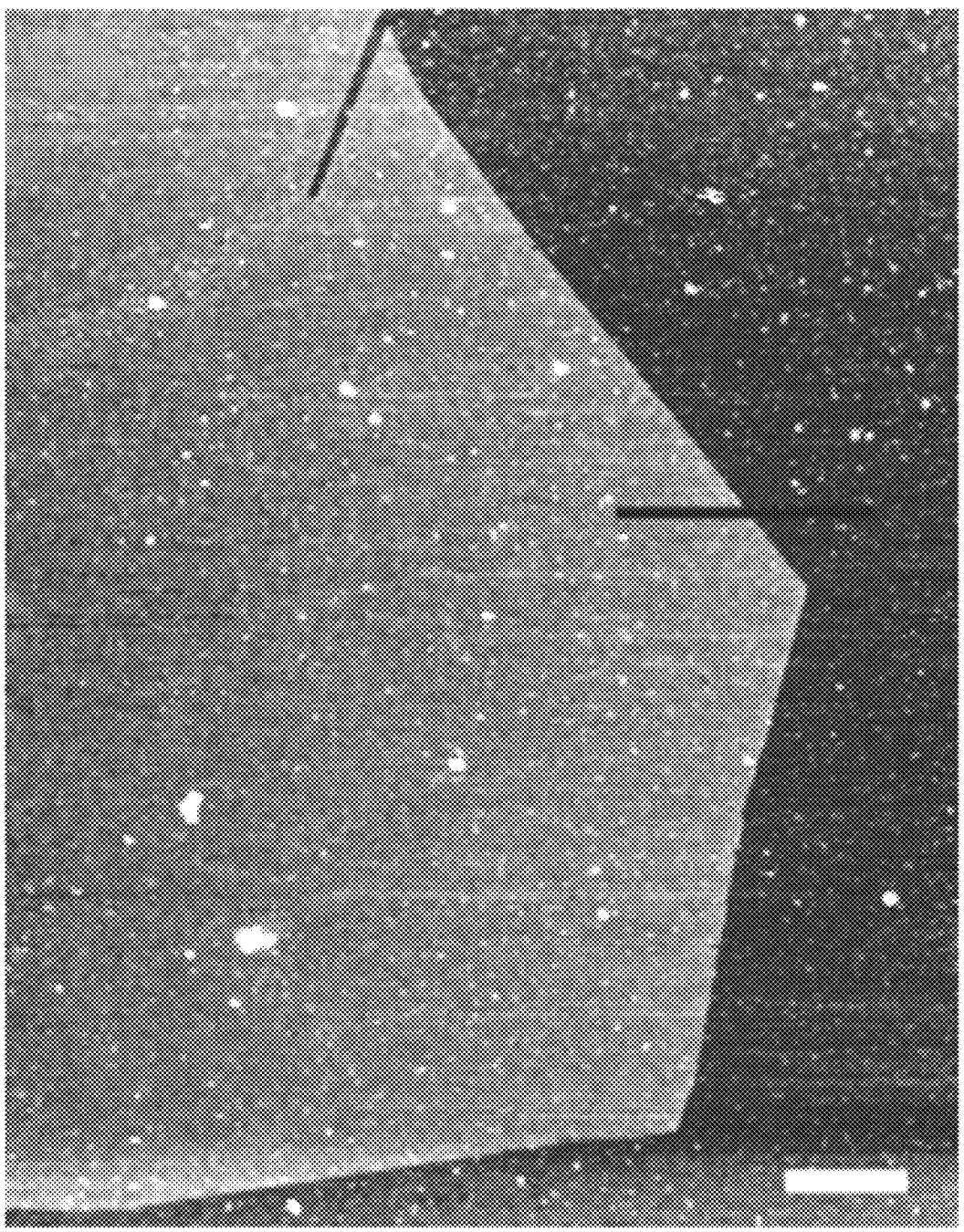

2.2 AFM of Graphene after All Functionalization Steps Except Incubation in Protein Solution FIGS. 5A and 5B are AFM scans of a graphene monolayer before (FIG. 5A) and after (FIG. 5B) all steps of attachment chemistry except for incubation in protein solution. The apparent height of the graphene in FIG. 5B is increased by ~1.8 nm, reflecting attachment of the NTA molecular layer, motivating the assignment in the main text, FIG. 1C and FIG. 12. Only a few particle-like features are observed, in agreement with the interpretation that particle like features in FIG. 1B are proteins linked to the graphene by their His-tag.

3. Control Experiments to Verify the Functionalization Scheme

3.1 Omission of Diazonium Incubation Step

Figure 6A:
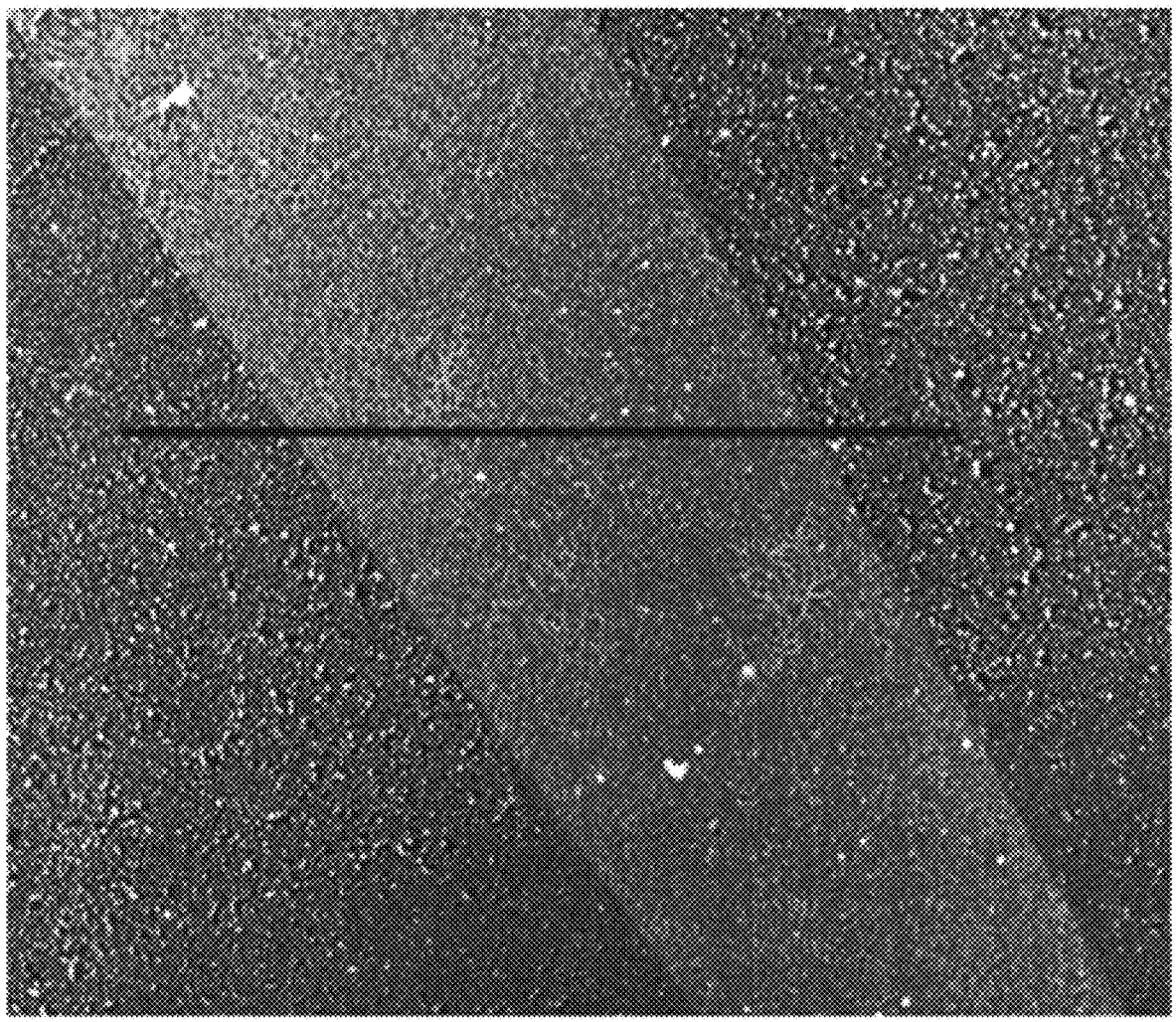
FIGS. 6A-6B presents FIG. 6A AFM image of a monolayer graphene after functionalization process where the diazonium incubation step was omitted and subsequent chemical steps were left unchanged. Z-scale is 15 nm.
Figure 6B:
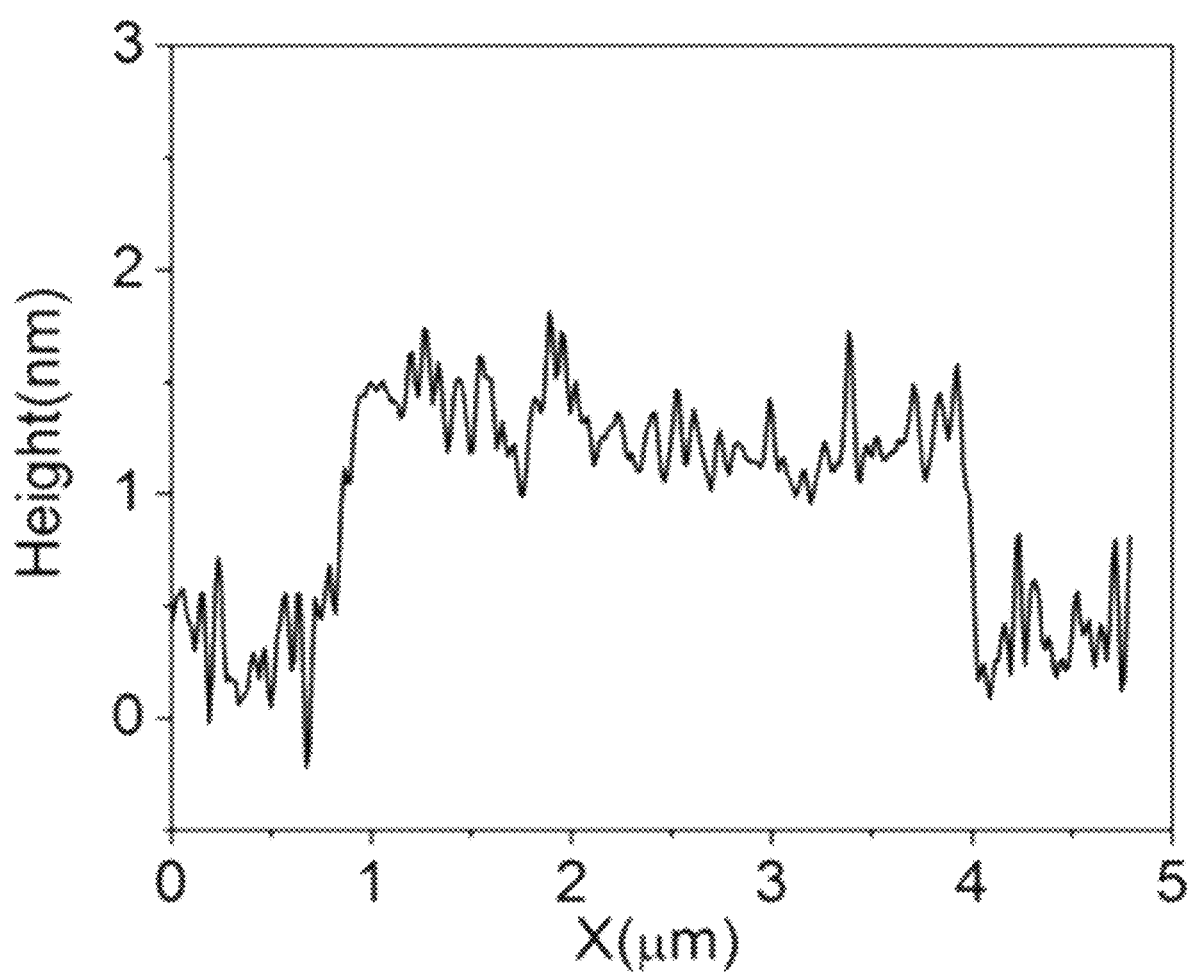

An experiment was conducted where the diazonium incubation step was omitted, while all other functionalization steps were conducted as previously described. FIG. 6A is an AFM image of the sample and FIG. 6B the associated line scan. The apparent graphene height is about 1.5 nm, only a slight increase above that expected for monolayer graphene (typically ~0.8-1 nm), perhaps due to a low-density residual layer of Ni-NTA molecules. No protein features are apparent. This control experiment demonstrates the necessity of the diazonium incubation for creation of active attachment sites on the graphene surface.

3.2 Use of a Non-His-Tagged Protein as a Negative Control

Figure 5C:
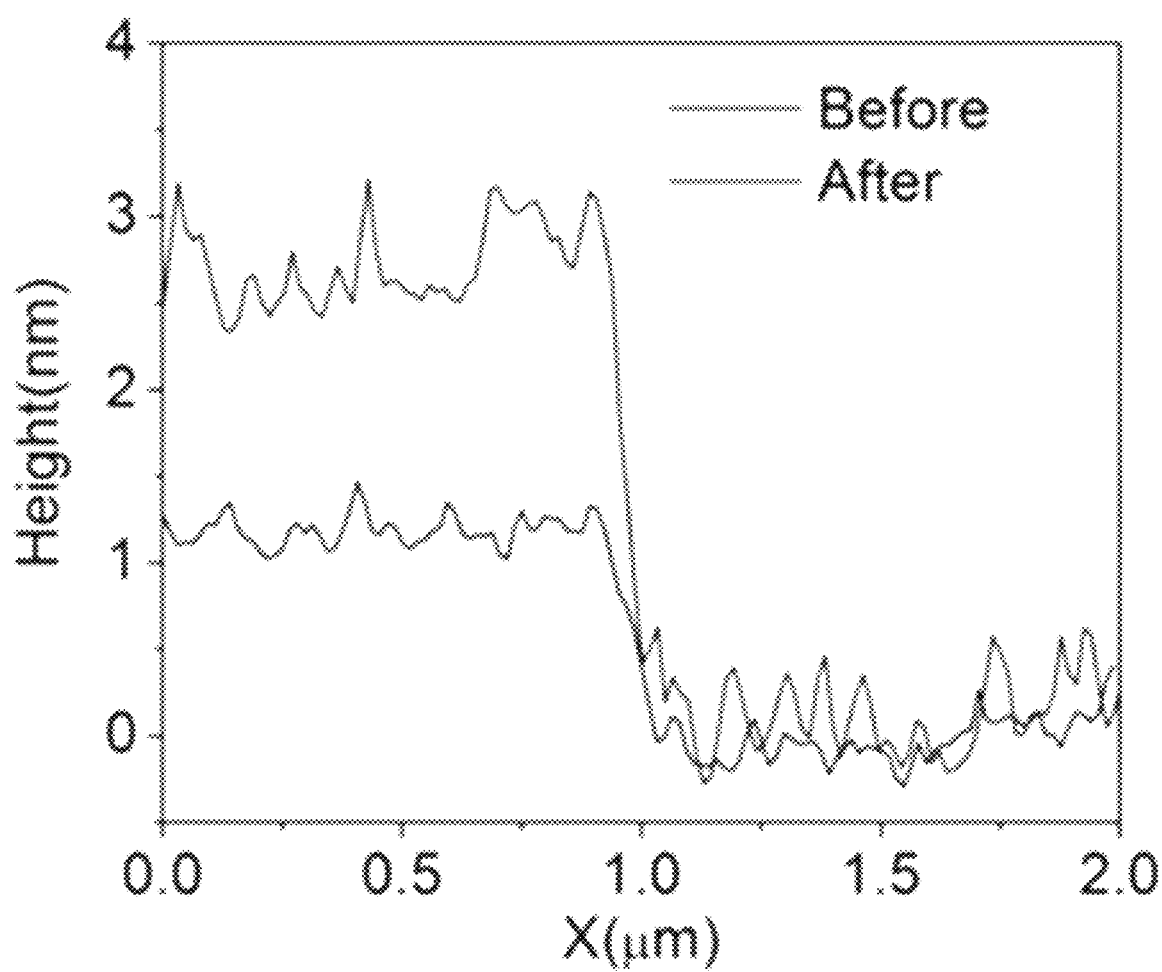
Figure 7A:
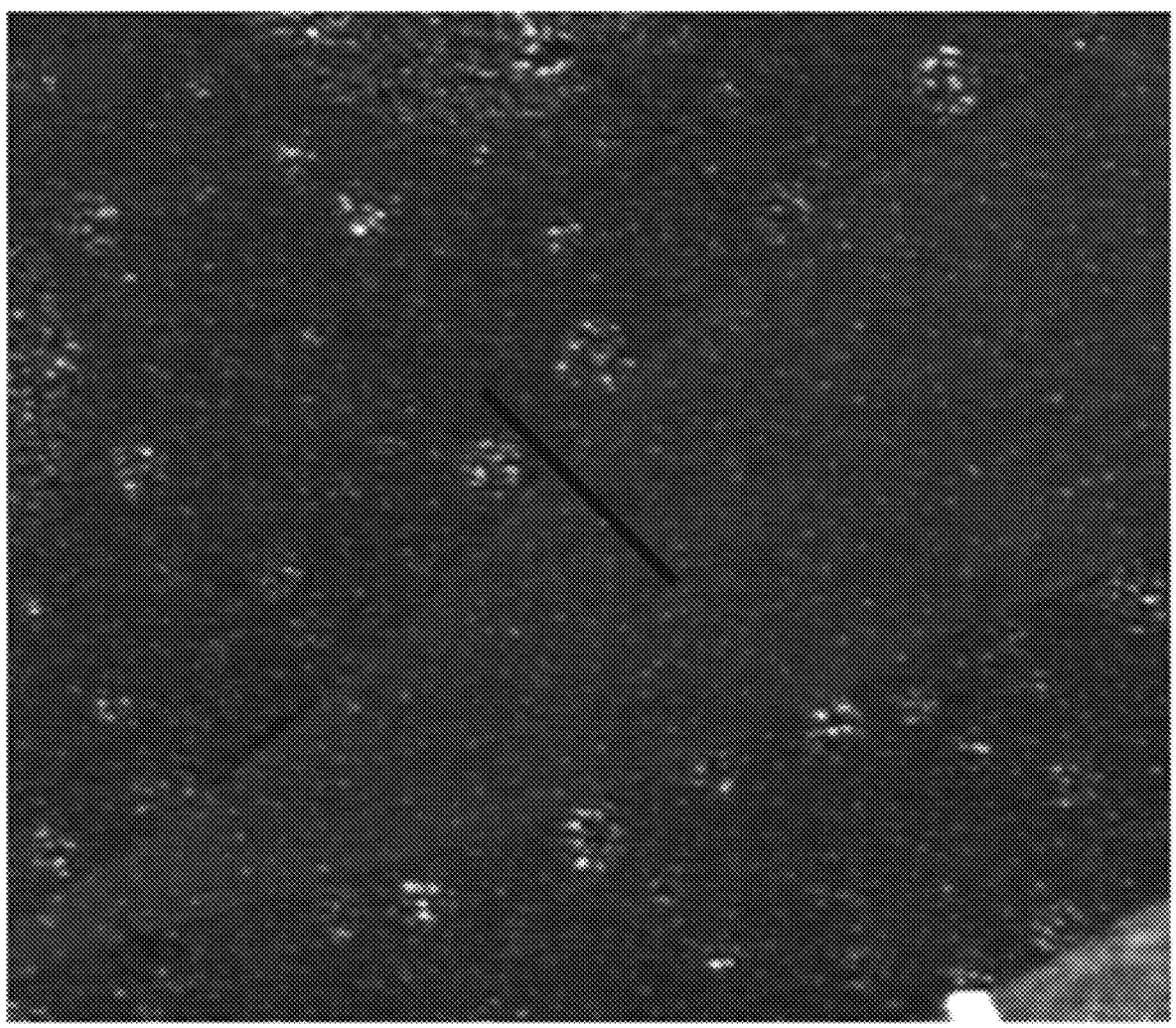
FIGS. 7A-7C. AFM images of a monolayer graphene FIG. 7A before and FIG. 7B after functionalization with a non-his-tag protein G. Z-axis scale is 15 nm.
Figure 7B:
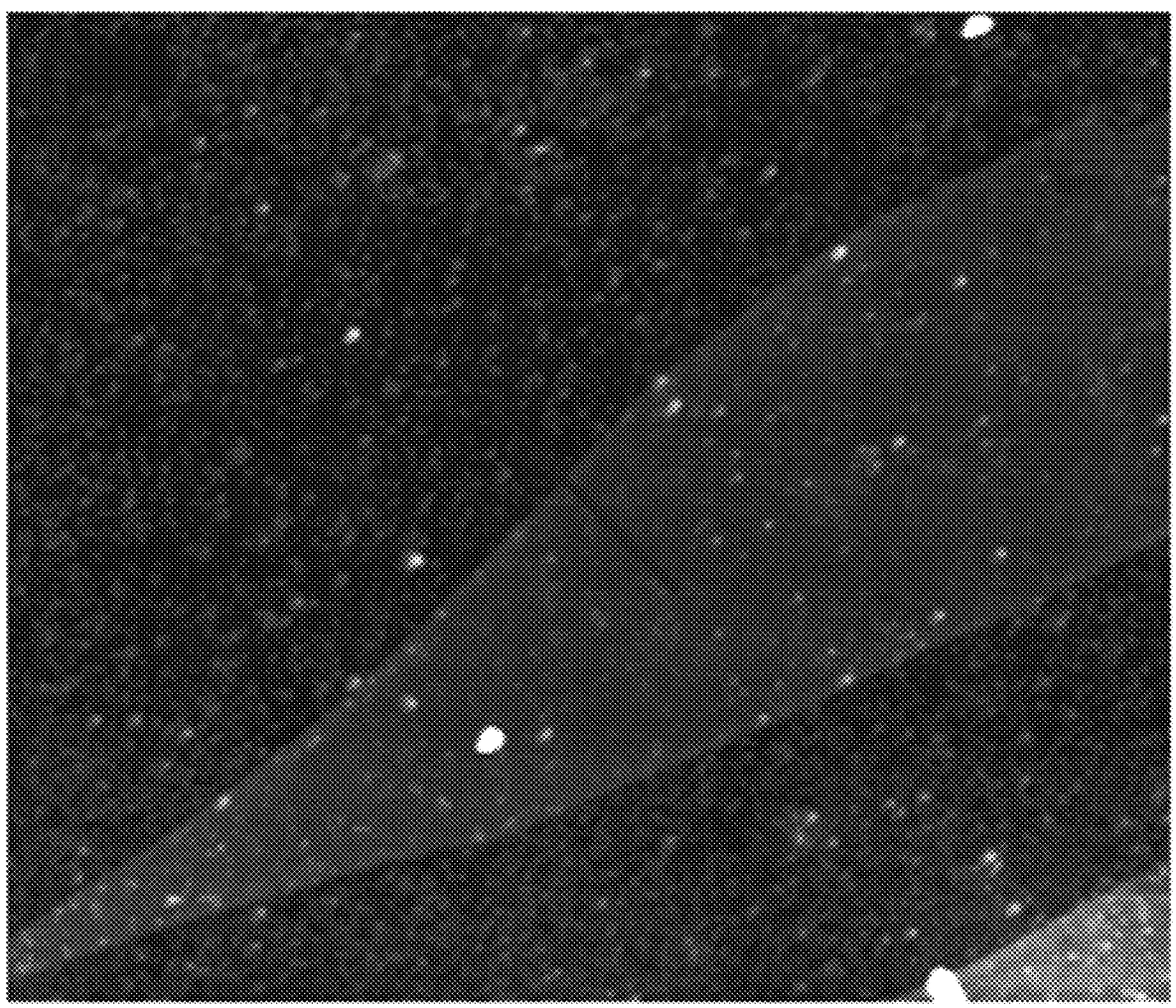
Figure 7C:
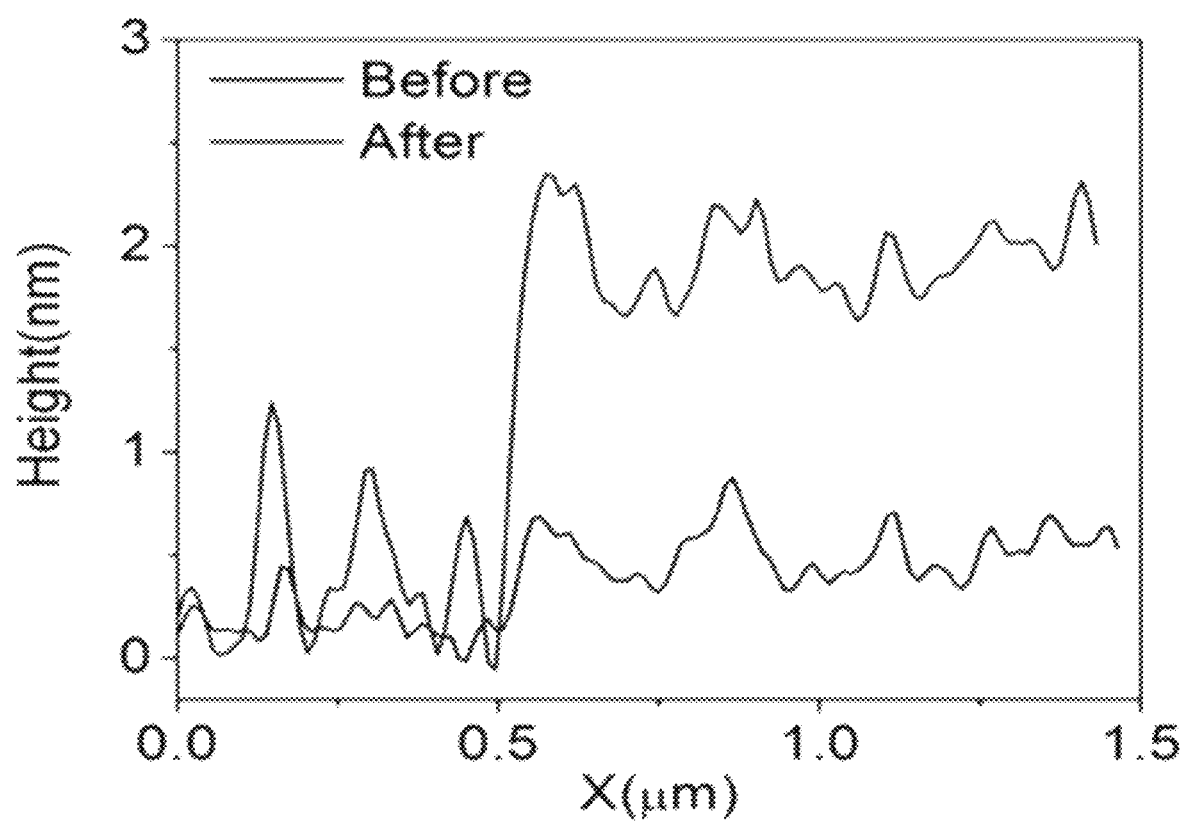

Graphene was functionalized as shown in FIG. 12, but a non-his-tagged protein-G (PRO-402, ProSpec Ltd) was used as a negative control. FIGS. 7A (FIG. 7B) is an AFM scan of graphene before (after) scan after functionalization. The apparent height of the graphene increased by ~1.8 nm, indicating the presence of an NTA monolayer (see FIGS. 5, 6A-6B above). No protein-like features were observed, providing evidence that protein attachment with controlled orientation occurs via the His-tag as indicated in FIG. 12.

4. Characterization by Raman Spectroscopy

4.1 Raman Spectroscopy of a Graphene after Diazonium Incubation

Figure 8A:
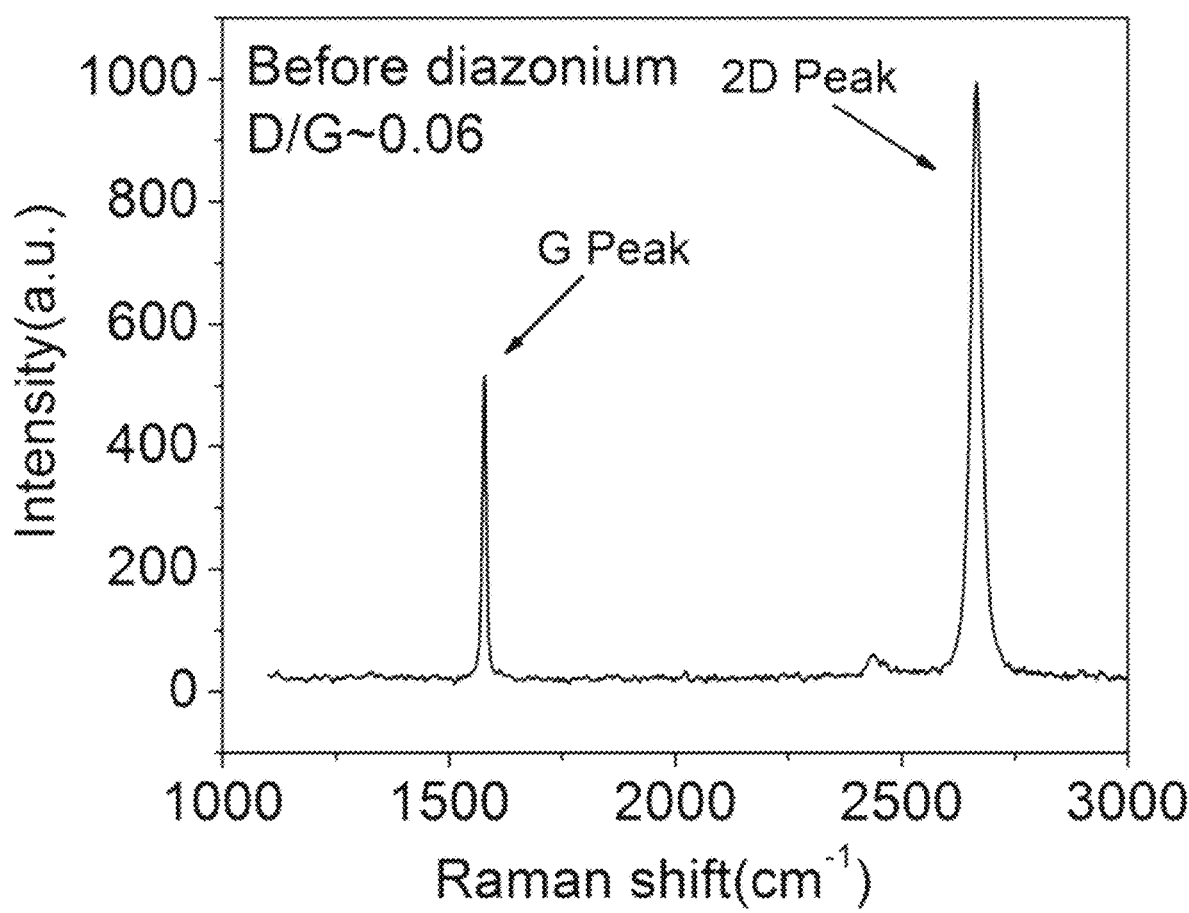
FIGS. 8A-8B presents FIG. 8A Raman spectrum of a pristine graphene and FIG. 8B Raman of the identical graphene after diazonium functionalization.

FIG. 8A is the Raman spectrum of a graphene monolayer, which shows essentially no D peak. FIG. 9B is the Raman spectrum of the same graphene layer after diazonium incubation. D/G ratio has increased by more than an order of magnitude after diazonium functionalization, indicative of a significant level of sp3 bonded carbon due to the decoration with carboxybenzene groups (see FIG. 12). similar to the result of graphene functionalized with protein.

Figure 8B:
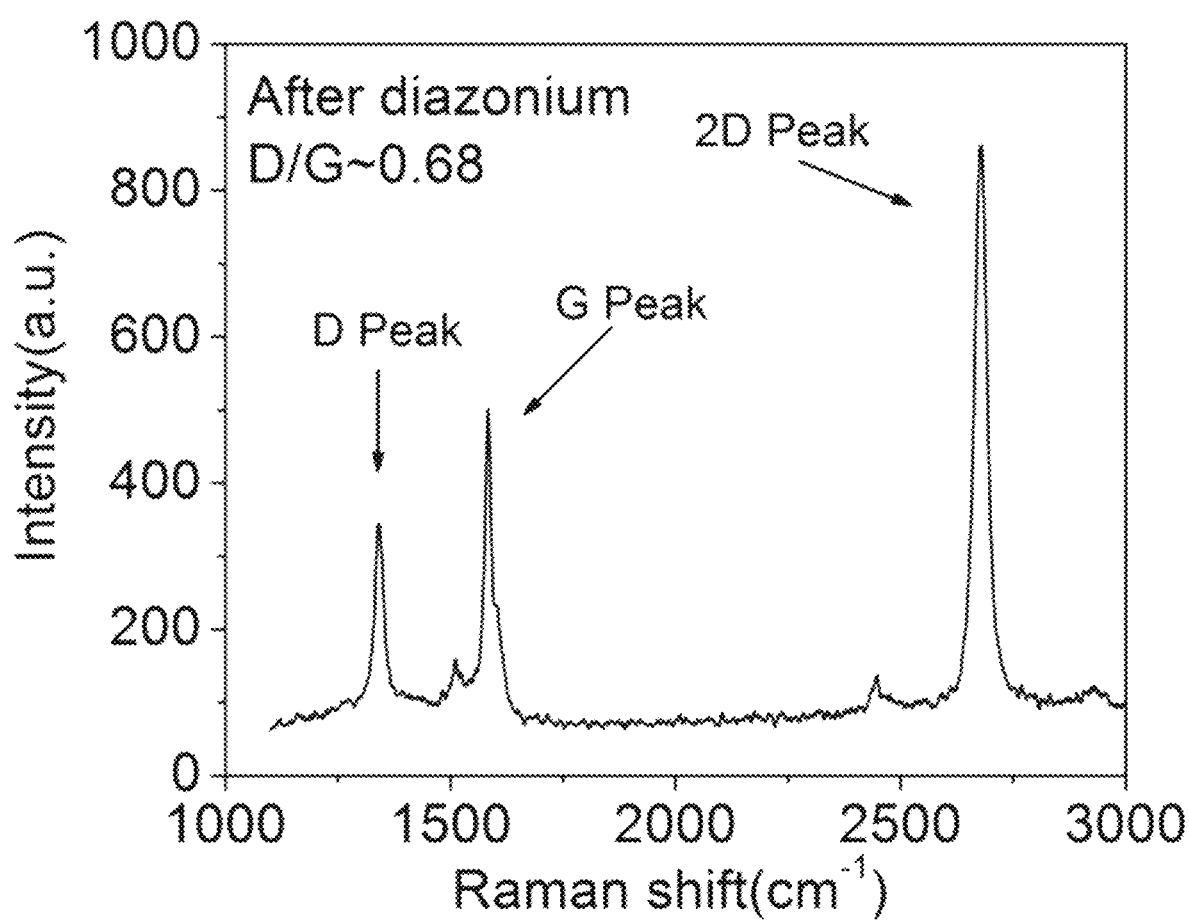
Figure 9A:
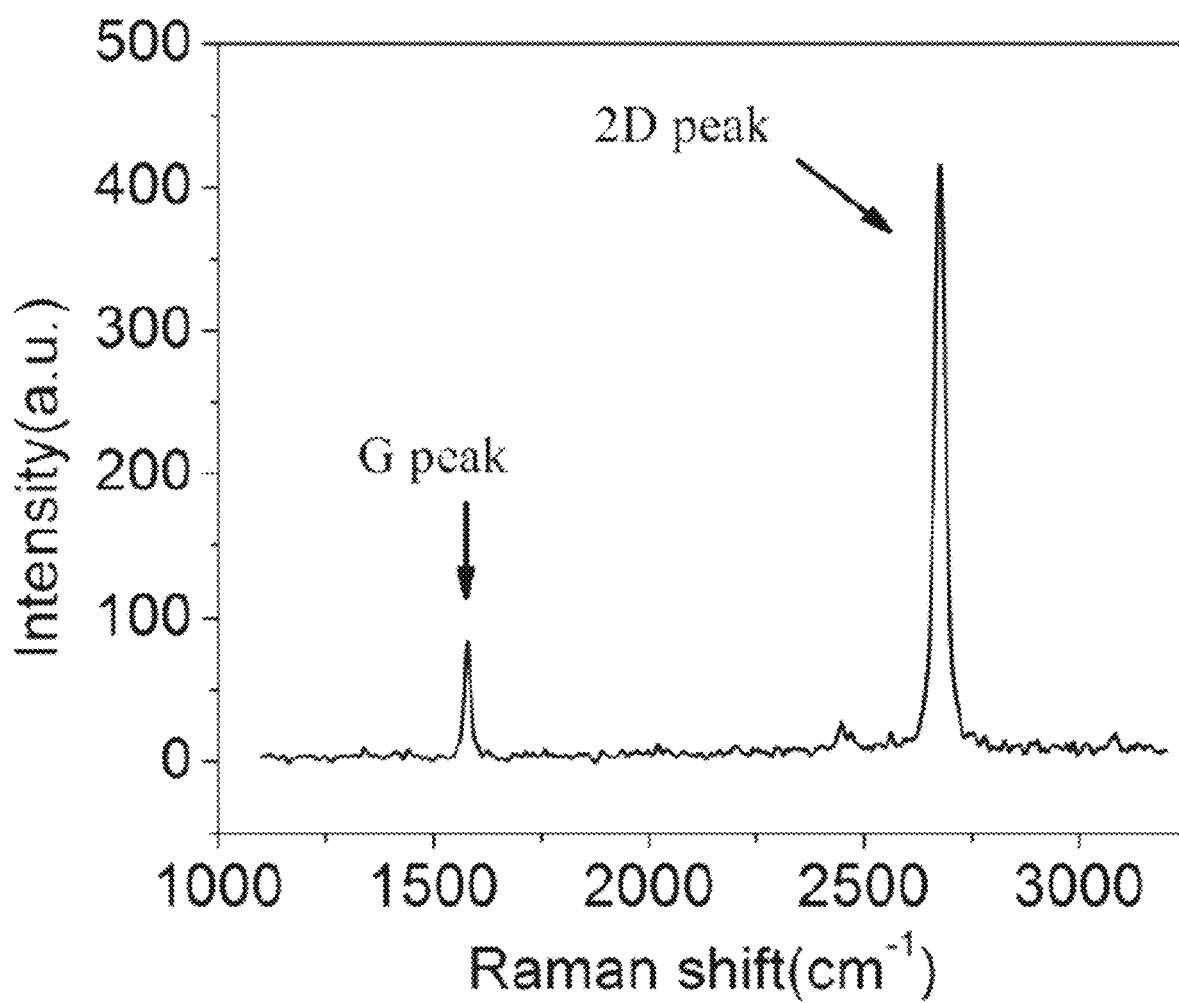
FIGS. 9A-9B presents Raman spectroscopy of monolayer graphene before FIG. 9A and after FIG. 9B functionalization with His-tagged protein G.
Figure 9B:
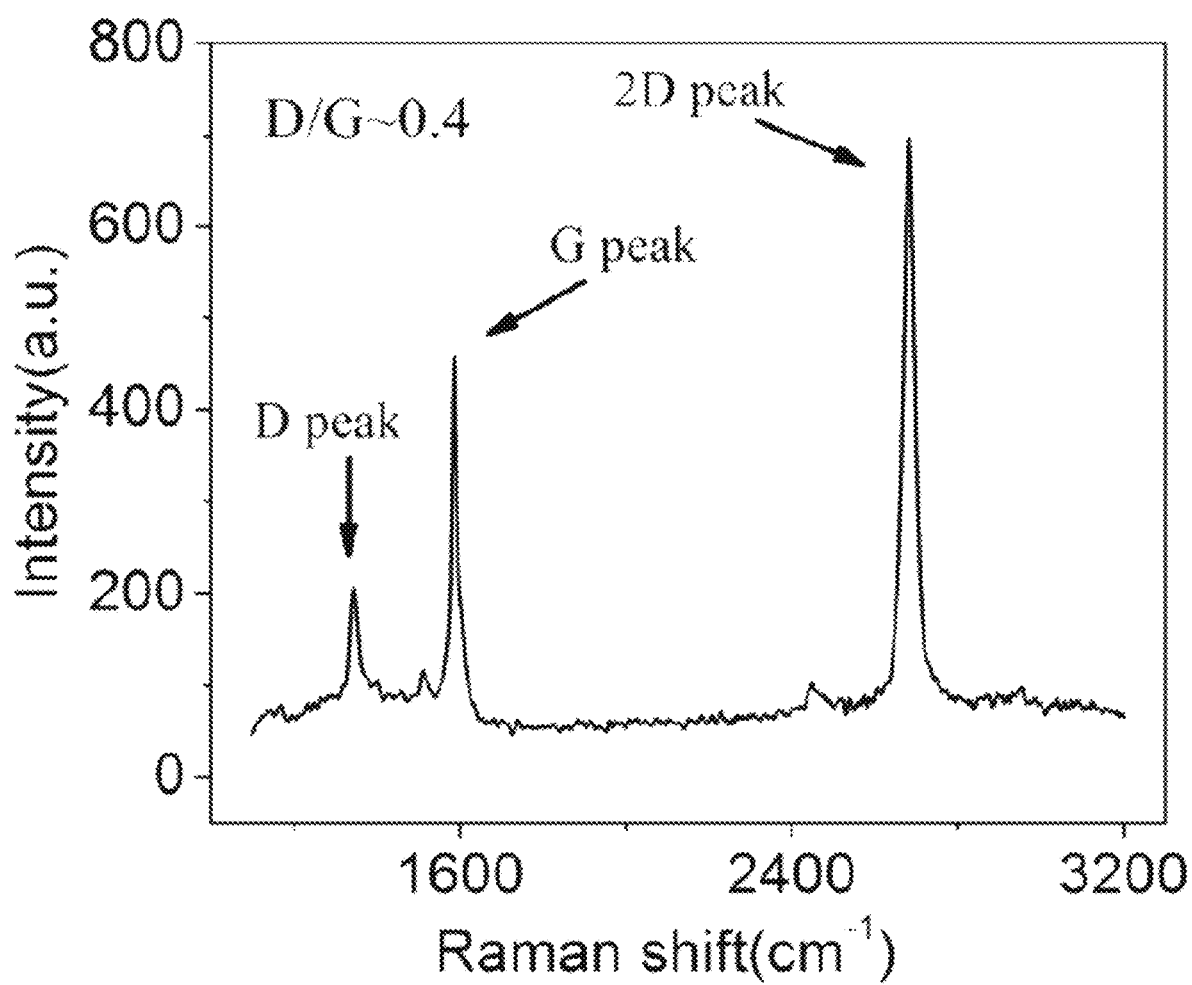

4.1 Raman Spectroscopy of a Graphene after Functionalization with His-Tagged Protein G FIGS. 9A-9B show the Raman spectra of a pristine graphene monolayer (FIG. 9A) and that of the same sample after functionalization with His-tagged protein G (FIG. 9B). The spectrum after functionalization is very similar to that after diazonium incubation (FIG. 8B), supporting the interpretation that the enhanced D peak reflects bond breaking of the sp2 graphene network.

Figure 10:
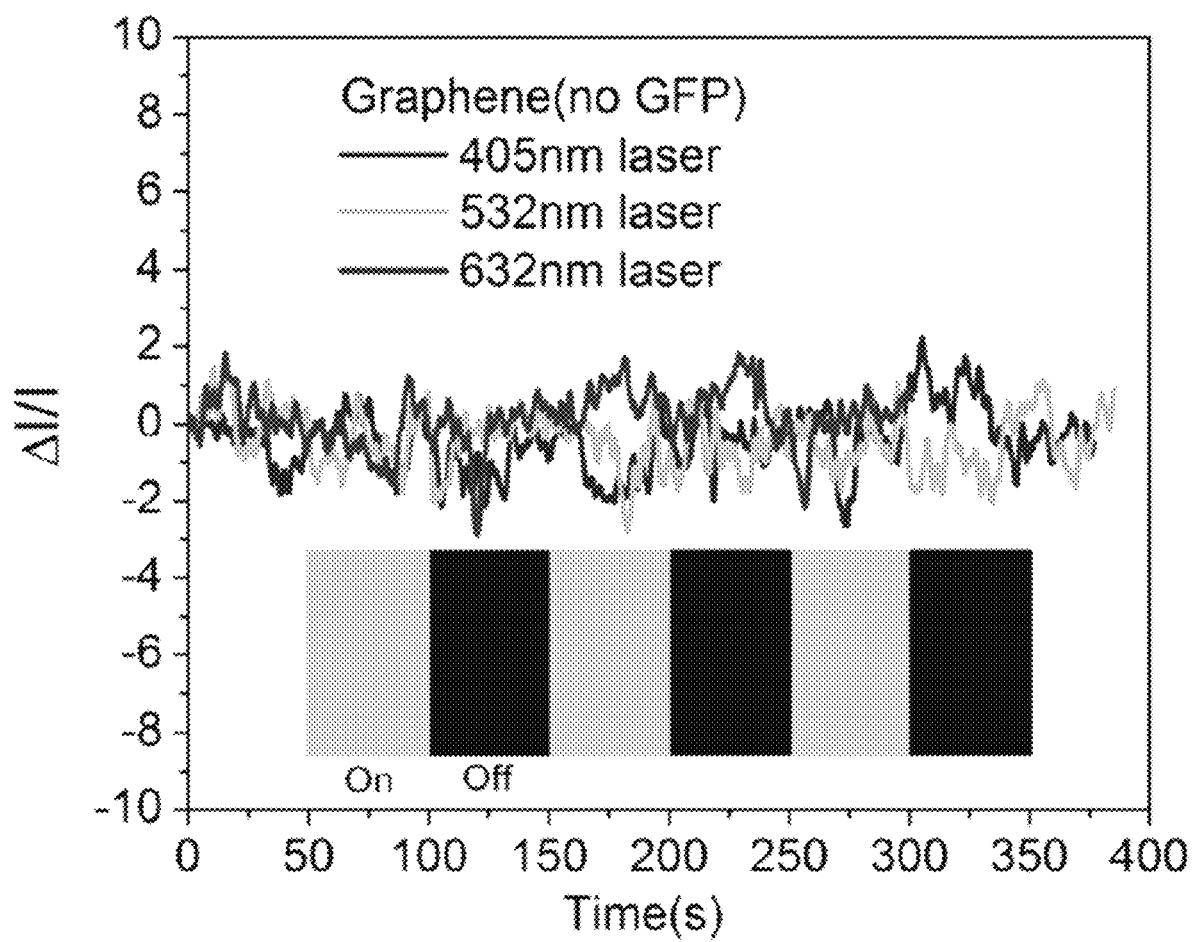
FIG. 10 illustrates a photocurrent responses of the graphene FET functionalized with diazonium and Ni-NTA but without with a fluorescent protein.

5. Photocurrent Response of Graphene FET (GFET) Functionalized with Diazonium and Ni-NTA but without Fluorescent Protein A GFET was fabricated and all functionalization steps in FIG. 12 were conducted except for a protein incubation step. FIG. 10 shows that the device had no detectable photocurrent response at any of the wavelengths used in these experiments. This provides confirmation of the interpretation in the text that photocurrent responses are derived from the optical absorption spectra of the fluorescent proteins used.

6. Measurement Demonstrating Device Lifetime of at Least Two Weeks

Figure 11:
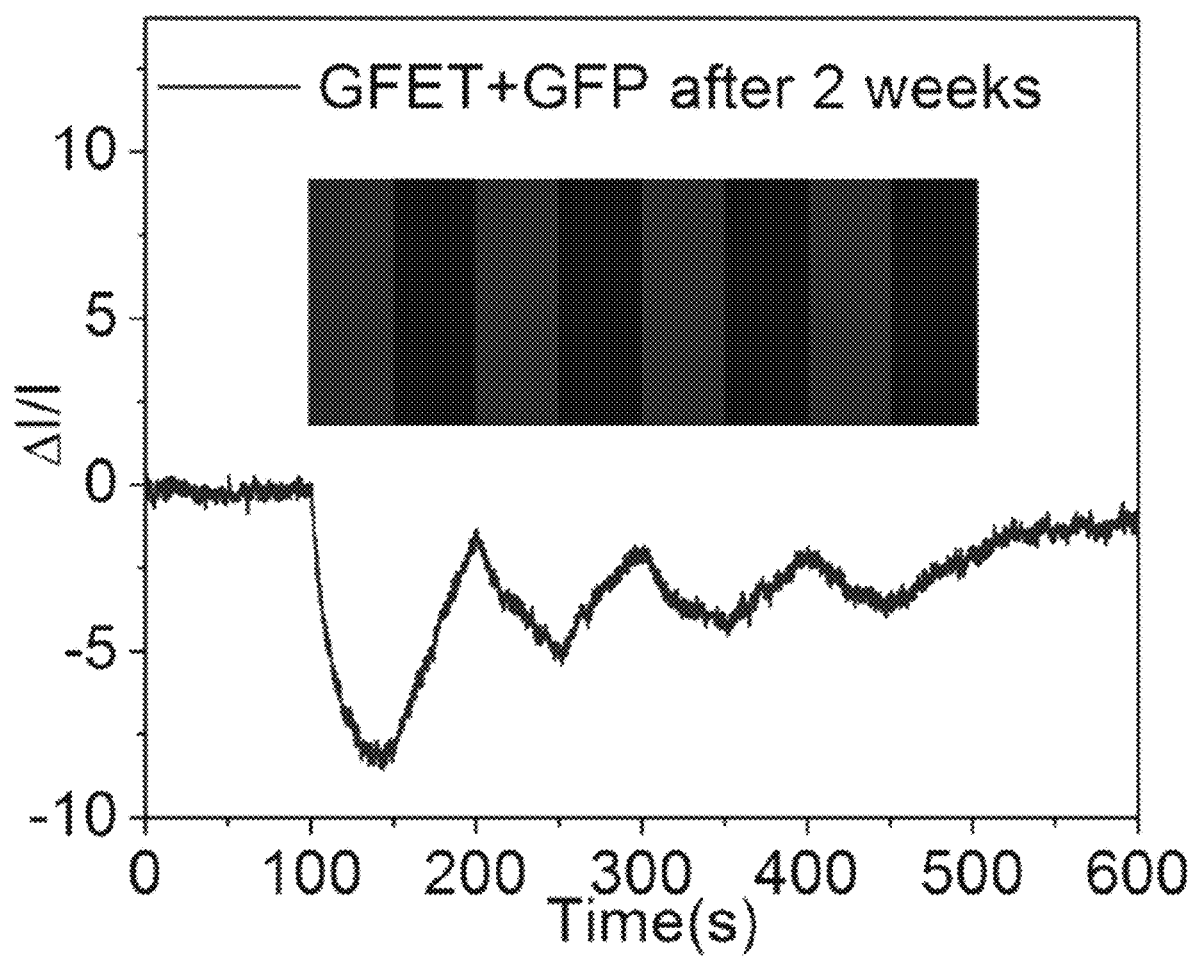
FIG. 11 illustrates a percentage change of current vs time of the same device measured after two weeks.

FIG. 11 shows the measured photocurrent responses of the same device in FIG. 3A in main text measured two weeks later. Device responses to violet illumination were essentially identical to those observed immediately after the device was fabricated, indicating little change in the behavior of the GFP-GFET hybrid on the two week timescale.

FURTHER REFERENCES

A. K. Geim and K. S. Novoselov, "The rise of graphene," Nature Materials 6, 183-191 (2007). Thomas Mueller, Fengnian Xia, and Phaedon Avouris, "Graphene photodetectors for high-speed optical communications," Nat Photon 4 (5), 297-301 (2010)

Fengnian Xia, Thomas Mueller, Yu-ming Lin et al., "Ultrafast graphene photodetector," Nat Nano 4 (12), 839-843 (2009)

Fengnian Xia, Thomas Mueller, Roksana Golizadeh-Mojarad et al., "Photocurrent Imaging and Efficient Photon Detection in a Graphene Transistor," Nano Letters 9 (3), 1039-1044 (2009)

Ming Liu, Xiaobo Yin, Erick Ulin-Avila et al., "A graphene-based broadband optical modulator," Nature 474 (7349), 64-67 (2011).

R. R. Nair, P. Blake, A. N. Grigorenko et al., "Fine Structure Constant Defines Visual Transparency of Graphene," Science 320 (5881), 1308-1308 (2008).

Y. Dan, Y. Lu, N. J. Kybert et al., "Intrinsic response of graphene vapor sensors," Nano Lett. 9, 1472-1475 (2009).

Richa Sharma, Joon Hyun Baik, Chrisantha J. Perera et al., "Anomalously Large Reactivity of Single Graphene Layers and Edges toward Electron Transfer Chemistries," Nano Letters 10 (2), 398-405 (2010).

B. R. Goldsmith, J. J. Mitala, J. Josue et al., "Biomimetic chemical sensors using nanoelectronic readout of olfactory receptor proteins," ACS Nano 5, 5408-5416 (2011)

R. A. Graff, T. M. Swanson, and M. S. Strano, "Synthesis of Nickel-Nitrilotriacetic acid coupled single-walled carbon nanotubes for directed self-assembly with polyhistidine-tagged proteins," Chem. Mater. 20, 1824-1829 (2008).

B. R. Lichtenstein, University of Pennsylvania, 2010.

Y. Lu, B. R. Goldsmith, N. J. Kybert et al., "DNA decorated graphene chemical sensors," Appl. Phys. Lett. 97, 083107 (2010).

Jian-Hao Chen, W. G. Cullen, C. Jong et al., "Defect Scattering in Graphene," Physical Review Letters 102 (23), 236805 (2009);

Z. H. Ni, L. A. Ponomarenko, R. R. Nair et al., "On Resonant Scatterers As a Factor Limiting Carrier Mobility in Graphene," Nano Letters 10 (10), 3868-3872 (2010).

Alexey M. Bogdanov, Alexander S. Mishin, Ilia V. Yampolsky et al., "Green fluorescent proteins are light-induced electron donors," Nat. Chem. Biol. 5 (7), 459-461 (2009).

What is claimed:

1. A device, comprising:
a biomolecule comprising a fluorescent protein having an optical absorption peak at around a particular wavelength of excitation illumination,
the biomolecule being in electronic communication with a graphene body so as to define a hybrid body,
the graphene body being in the form of a flat single-atom thick sheet,
the hybrid body having a photocurrent response at the particular wavelength of excitation illumination;
a monitor configured to monitor the photocurrent response of the hybrid body; and
a source of illumination configured to deliver illumination at around the particular wavelength of excitation illumination.

2. The device of claim 1, wherein the protein comprises a histidine tag.

3. The device of claim 1, wherein the protein is bound to the graphene body by a peptide sequence.

4. The device of claim 1, wherein the protein comprises a reactive amino acid.

5. The device of claim 1, wherein the graphene comprises Diimide-activated amidation.

6. The device of claim 1, further comprising a cysteine-graphene linkage.

7. The device of claim 1, whether comprising an amide bond between the protein and graphene, an imine bond between the protein and graphene, a thiourea bond between the protein and graphene, an aminoalcohol bond between the protein and graphene.

8. The device of claim 1, wherein the fluorescent protein comprises a green fluorescent protein, a yellow fluorescent protein, a red fluorescent protein, a cyan fluorescent protein, or any combination thereof.

9. The device of claim 1, wherein the fluorescent protein comprises a fluorescent redox cofactor.

10. The device of claim 1, further comprising a flavoprotein, a heme containing protein wherein an iron has been substituted by zinc, or any combination thereof.

11. The device of claim 1, wherein the fluorescent protein comprises tryptophan.

12. The device of claim 1, wherein the electronic communication between the biomolecule and the graphene body includes an interaction between a nickel-nitriloacetic acid group and a histidine residue.

13. The device of claim 1, wherein the particular wavelength of excitation illumination is a wavelength between about 1 nm and about 900 nm.

14. A device, comprising:
a graphene body in the form of a flat single-atom thick sheet in electronic communication with a biomolecule that preferentially binds to a binding partner, thereby forming a hybrid body,
the biomolecule comprising a green fluorescent protein, a yellow fluorescent protein, a red fluorescent protein, a cyan fluorescent protein, or any combination thereof,
the hybrid body exhibiting a measureable photocurrent response when the biomolecule binds to the binding partner.

15. The device of claim 1, further comprising a plurality of biomolecules having different absorption peaks in electronic communication with the graphene body.

16. The device of claim 14, wherein further comprising a plurality of biomolecules having different binding partners in electronic communication with the graphene body.

17. The device of claim 1, further comprising a fusion protein.

18. The device of claim 1, further comprising a chitin binding protein, a maltose binding protein, glutathione-S-transferase, an epitope tag, or any combination thereof.

* * * * *